(12) United States Patent
Phan et al.

(10) Patent No.: US 6,710,034 B2
(45) Date of Patent: Mar. 23, 2004

(54) 5-O-MYCAMINOSYLTYLONIDE DERIVATIVES

(75) Inventors: Ly Tam Phan, Malden, MA (US); Nha Vo, Malden, MA (US); Yat Sun Or, Cambridge, MA (US); Yao-Ling Qiu, Somerville, MA (US); Ying Hou, Everett, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/125,840

(22) Filed: Apr. 19, 2002

(65) Prior Publication Data

US 2003/0203858 A1 Oct. 30, 2003

(51) Int. Cl.$^7$ .......................... A61K 31/70; C07H 17/08
(52) U.S. Cl. .......................... 514/30; 536/7.1; 536/18.5
(58) Field of Search ............................. 536/7.1; 514/30

(56) References Cited

U.S. PATENT DOCUMENTS

| | | | |
|---|---|---|---|
| 4,436,729 A | 3/1984 | Ganguly et al. | 536/7.1 |
| 4,468,511 A | 8/1984 | Kirst et al. | 536/7.1 |
| 4,579,940 A | 4/1986 | Watanabe et al. | |
| 4,629,786 A | 12/1986 | Debono et al. | 536/7.1 |

FOREIGN PATENT DOCUMENTS

| | | | |
|---|---|---|---|
| WOPCT/IB | WO 95/02594 | 1/1995 | C07D/407/12 |
| WO | WO 03/011882 A1 | 2/2003 | C07H/17/08 |

OTHER PUBLICATIONS

S. Sakamoto et al.: "Synthesis of 23–C Substituted Derivatives of Mycaminosyl Tylonolide and 4'–Deoxymycaminosyl Tylonolide." Bulletin of The Chemical Society of Japan, vol. 60, No. 1, 1987, pp. 355–363, XP008019150 p. 356, column 2, table, compound 10.

K. Kiyoshima et al.: "Structure–Activity Relationship Studies on 4"–0–Acyltylosin Derivatives: Significance of their 23–0–Mycinosyl and 4"–0–Acyl Moieties in Antimicrobial Activity Against Macrolide–Resistant Microbes." Journal of Antibiotics, vol. 42, No. 11, 1989, pp. 1661–1672, XP008019141.

*Primary Examiner*—Elli Peselev
(74) *Attorney, Agent, or Firm*—Gaetano Maccarone; Jason O. Ferrone

(57) ABSTRACT

There are described novel 5-O-mycaminosyltylonide derivatives and pharmaceutically acceptable compositions comprising a therapeutically effective amount of a compound of the invention in combination with a pharmaceutically acceptable carrier. Also described are a method for treating bacterial infections by administering to an animal a pharmaceutical composition containing a therapeutically-effective amount of a compound of the invention, and processes for the preparation of such compounds.

17 Claims, No Drawings

5-O-MYCAMINOSYLTYLONIDE DERIVATIVES

REFERENCE TO RELATED APPLICATION

Reference is made to copending, commonly assigned U.S. patent application Ser. No. 10/126,076, filed on even date herewith.

TECHNICAL FIELD

The present invention relates to novel macrolides having antibacterial activity that are useful in the treatment and prevention of bacterial infections. More particularly, the present invention relates to a novel class of 16-membered macrolide compounds, compositions containing them, methods for using and processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic families (14-, 15- and 16-membered ring derivatives) exhibit a wide range of characteristics (antibacterial spectrum, side-effects and bioavailability). Among the commonly used macrolides are erythromycin and josamycin.

The 16-membered ring macrolide antibiotics constitute an important clinically useful series of naturally occurring compounds within the macrolide class of antibiotics, as they show some advantages over 14-membered ring compounds (gastrointestinal tolerance and activity against strains expressing resistance of the inducible type). Sixteen membered macrolides usually contain an amino disaccharide-4-O-(L-mycarosyl)-D-mycaminose and/or D-desosamine. One class has only neutral sugars. The sixteen membered macrolides can be classified into two major series—leucomycin and tylosin series.

The tylosin series is divided into two groups—IIA and IIB—which differ at the C-6-side chain and the nature of the sugars on the chromophore. Tylosin consists of a substituted 16-membered ring lactone (tylonolide), an aminosugar (D-mycaminose) attached to C-5, two neutral sugars (D-mycinose attached at C-23 and L-mycarose attached at C-4') and an acetaldehyde at C-6.

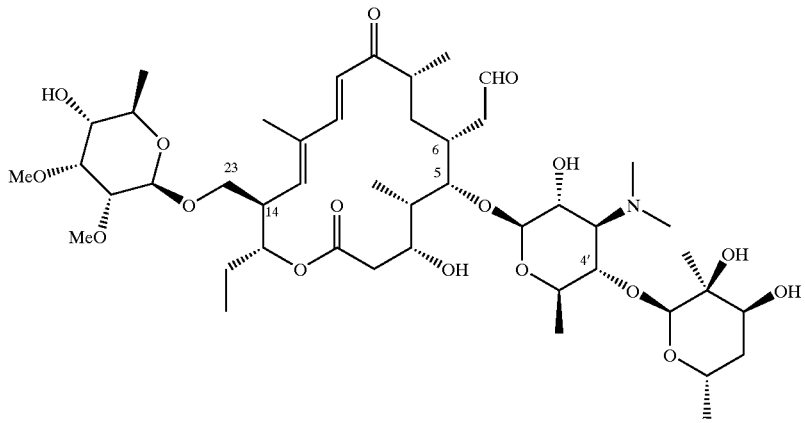

Tylosin

Considerable research efforts have been carried out on tylosin and its derivatives but not much success has been observed with this subclass. In addition to improving the overall profile of the macrolides in terms of acid stability, tolerance and pharmacokinetics, the search for macrolides active against $MLS_B$-resistant strains ($MLS_B$=Macrolides-Lincosamides-Type B Streptogramines) has become a major goal.

SUMMARY OF THE INVENTION

The present invention provides a novel class of 5-O-mycaminosyltylonide (OMT) analogs possessing increased antibacterial activity toward Gram positive and Gram negative bacteria as well as macrolide resistant Gram positives. In addition, the present invention provides a class of 5-O-mycaminosyltylonide derivatives that are more acid stable and overcome bacterial resistance.

In one embodiment, the present invention provides compounds represented by Formula I, or a pharmaceutically acceptable salt, ester or prodrug thereof:

(I)

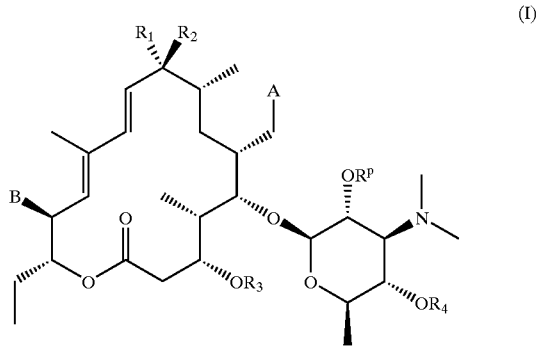

In Formula I,
A is selected from the group consisting of:
(1) —CHO or a protected aldehyde;
(2) —CN;
(3) —CH=N—NR$_5$R$_6$, wherein R$_5$ and R$_6$ are each independently selected from the group consisting of:
  (a) hydrogen;
  (b) C$_1$–C$_6$-alkyl, optionally substituted with one or more substituents selected from the group consisting of: halogen, aryl, substituted aryl, heterocyclic and substituted heterocyclic;
  (c) C$_2$–C$_6$-alkenyl, optionally substituted with one or more substituents selected from the group consisting of: halogen, aryl, substituted aryl, heterocyclic and substituted heterocyclic;
  (d) C$_2$–C$_6$-alkynyl, optionally substituted with one or more substituents selected from the group consisting: of halogen, aryl, substituted aryl, heterocyclic and substituted heterocyclic; and
  (e) R$_5$ and R$_6$ taken together with the nitrogen atom to which they are connected to form a 3- to 7-membered ring which may optionally contain one or more heterofunctions selected from the group consisting of: —O—, —NH—, —N(C$_1$–C$_6$-alkyl)-, —N(aryl)-, —N(heteroaryl)-, —S—, —S(O)— and —S(O)$_2$—;
(4) —CH=N—OR$_5$, wherein R$_5$ is as previously defined;
(5) —CH$_3$X, wherein X is selected from the group consisting of:
  (a) hydroxy or protected hydroxy;
  (b) halogen;
  (c) —NR$_5$R$_6$, where R$_5$ and R$_6$ are as previously defined;
  (d) —NR$_5$C(O)—R$_7$, where R$_5$ is as previously defined and R$_7$ is selected from the group consisting of:
    i. hydrogen;
    ii. C$_1$–C$_6$-alkyl, optionally substituted with one or more substituents selected from the group consisting of: halogen, aryl, substituted aryl, heterocyclic and substituted heterocyclic;
    iii. C$_2$–C$_6$-alkenyl, optionally substituted with one or more substituents selected from the group consisting of: halogen, aryl, substituted aryl, heterocyclic and substituted heterocyclic;
    iv. C$_2$–C$_6$-alkynyl, optionally substituted with one or more substituents selected from the group consisting of: halogen, aryl, substituted aryl, heterocyclic and substituted heterocyclic;
    v. aryl;
    vi. substituted aryl;
    vii. heterocyclic; and
    viii. substituted heterocyclic;
  (e) —NR$_5$C(O)—NR$_6$R$_7$, where R$_5$, R$_6$, and R$_7$ are as previously defined;
  (f) —NR$_5$—NR$_6$R$_7$, where R$_5$, R$_6$ and R$_7$ are as previously defined;
  (g) —NR$_5$—NR$_6$C(O)—R$_7$, where R$_5$, R$_6$ and R$_7$ are as previously defined;
  (h) —S(O)$_n$—R$_8$, where R$_8$ is selected from the group consisting of: aryl, substituted aryl, heterocyclic and substituted heterocyclic, where n=0, 1 or 2;
  (i) —S(O)$_n$—(C$_1$–C$_6$-alkyl), optionally substituted with one or more substituents selected from the group consisting of: halogen, aryl, substituted aryl, heterocyclic and substituted heterocyclic, where n is as previously defined;
  (j) —S(O)$_n$—(C$_2$–C$_6$-alkenyl), optionally substituted with one or more substituents selected from the group consisting of: halogen, aryl, substituted aryl, heterocyclic and substituted heterocyclic, where n is as previously defined;
  (k) —S(O)$_n$—(C$_2$–C$_6$-alkynyl), optionally substituted with one or more substituents selected from the group consisting of: halogen, aryl, substituted aryl, heterocyclic and substituted heterocyclic, where n is as previously defined; and
  (l) —O—M—Y, where M is:
    i. absent,
    ii. —C(O)—,
    iii. —C(O)N(R$_5$)—, where R$_5$ is as previously defined,
    iv. —C$_1$–C$_6$-alkyl-N(R$_5$)—, where R$_5$ is as previously defined,
    v. —C$_2$–C$_6$-alkenyl-N(R$_5$)—, where R$_5$ is as previously defined, or
    vi. —C$_2$–C$_6$-alkynyl-N(R$_5$)—, where R$_5$ is as previously defined, and Y is:
      i. hydrogen,
      ii. C$_1$–C$_6$-alkyl, optionally substituted with one or more substituents selected from the group consisting of: halogen, —OR$_5$, aryl, substituted aryl, heterocyclic and substituted heterocyclic, where R$_5$ is as previously defined,
      iii. C$_2$–C$_6$-alkenyl, optionally substituted with one or more substituents selected from the group consisting of: halogen, —OR$_5$, aryl, substituted aryl, heterocyclic and substituted hetreocyclic, where R$_5$ is as previously defined,
      iv. C$_2$–C$_6$-alkynyl, optionally substituted with one or more substituents selected from the group consisting of: halogen, —OR$_5$, aryl, substituted aryl, heterocyclic and substituted heterocyclic, where R$_5$ is as previously defined,
      v. aryl,
      vi. substituted aryl,
      vii. heterocyclic, or
      viii. substituted heterocyclic; and
(6) heterocyclic or substituted heterocyclic;
B is selected from the group consisting of:
(1) —CHO or a protected aldehyde;
(2) —CN;
(3) —CH=N—NR$_5$R$_6$, wherein R$_5$ and R$_6$ are as previously defined;
(4) —CH=N—OR$_5$, wherein R$_5$ is as previously defined;
(5) —CH$_2$Z, wherein Z is selected from the group consisting of:
  (a) halogen;
  (b) —NR$_5$C(O)—R$_7$, where R$_5$ and R$_7$ are as previously defined;
  (c) —NR$_5$C(O)—NR$_6$R$_7$, where R$_5$, R$_6$, and R$_7$ are as previously defined;
  (d) —NR$_5$—NR$_6$R$_7$, where R$_5$, R$_6$ and R$_7$ are as previously defined;
  (e) —NR$_5$—NR$_6$C(O)—R$_7$, where R$_5$, R$_6$ and R$_7$ are as previously defined;
  (f) —S(O)$_n$—R$_8$, where R$_8$ and n are as previously defined;
  (g) —S(O)$_n$—(C$_1$–C$_6$-alkyl), optionally substituted with one or more substituents selected from the group consisting of: halogen, aryl, substituted aryl, heterocyclic and substituted heterocyclic, where n is as previously defined;

(h) —S(O)$_n$—(C$_2$–C$_6$-alkenyl), optionally substituted with one or more substituents selected from the group consisting of: halogen, aryl, substituted aryl, heterocyclic and substituted heterocyclic, where n is as previously defined;

(i) —S(O)$_n$—(C$_2$–C$_6$-alkynyl), optionally substituted with one or more substituents selected from the group consisting of: halogen, aryl, substituted aryl, heterocyclic and substituted heterocyclic, where n is as previously defined; and (j) —NR$_9$R$_{10}$, where R$_9$ and R$_{10}$ are each independently selected from the group consisting of:
  i. hydrogen;
  ii. C$_1$–C$_6$-alkyl, optionally substituted with one or more substituents selected from the group consisting of: halogen, aryl, substituted aryl, heterocyclic, —O—R$_5$ and —NR$_5$R6, where R$_5$ and R$_6$ are as previously defined;
  iii. C$_2$–C$_6$-alkenyl, optionally substituted with one or more substituents selected from the group consisting of: halogen, aryl, substituted aryl, heterocyclic, substituted heterocyclic, —O—R$_5$ and —NR$_5$R$_6$, where R$_5$ and R$_6$ are as previously defined;
  iv. C$_2$–C$_6$-alkynyl, optionally substituted with one or more substituents selected from the group consisting of: halogen, aryl, substituted aryl, heterocyclic, substituted heterocyclic, —O—R$_5$ and —NR$_5$R$_6$, where R$_5$ and R$_6$ are as previously defined; and
  v. —W—R$_{11}$, where W is selected from the group consisting of:
    1. —C(O)—;
    2. —C(O)O—;
    3. —C(S)—;
    4. —C(S)—S—;
    5. —C(S)—O—;
    6. —C(S)—N(R$_5$)—, where R$_5$ is as previously defined;
    7. —C(O)N(R$_5$)—, where R$_5$ is as previously defined;
    8. —C(=NR$_5$)—O—, where R$_5$ is as previously defined; and
    9. —C(=NR$_{11}$)—NR$_5$R$_6$, where R$_5$ and R$_6$ are as previously defined and where R$_{11}$ is selected from thp group consisting of:
      a. hydrogen;
      b. C$_1$–C$_6$-alkyl, optionally substituted with one or more substituents selected from the group consisting of: halogen, aryl, substituted aryl, heterocyclic and substituted heterocyclic;
      c. C$_2$–C$_6$-alkenyl, optionally substituted with one or more substituents selected from the group consisting of: halogen, aryl, substituted aryl, heterocyclic and substituted heterocyclic; and
      d. C$_2$–C$_6$-alkynyl, optionally substituted with one or more substituents selected from the group consisting of: halogen, aryl, substituted aryl, heterocyclic and substituted heterocyclic;
  vi. R$_9$ and R$_{10}$, taken together with the nitrogen atom to which they are attached, represent the carbon or hetero atoms necessary to form a heterocyclic or substituted heterocyclic moiety; and
  vii. R$_9$ and R$_{10}$, taken together with the nitrogen atom to which they are attached, form a 4 to 8 membered ring which contains one or more W moieties, and optionally may contain one or more heteromoieties selected from the group consisting of: —O—, —S—, —S(O)$_2$— and —NR$_5$—, where W and R$_5$ are as previously defined;

R$_1$ and R$_2$ are each independently selected from the group consisting of:
  (1) hydrogen;
  (2) hydroxy;
  (3) protected hydroxy;
  (4) —OC(O)—(C$_1$–C$_{12}$-alkyl), optionally substituted with one or more substituents selected from the group consisting of: halogen, aryl, substituted aryl, heterocyclic, substituted heterocyclic, —OR$_5$ and —NR$_5$R$_6$ where R$_5$ and R$_6$ are as previously defined;
  (5) —OR$_5$, where R$_5$ is as previously defined;
  (6) halogen;
  (7) —NR$_5$R$_6$, where R$_5$ and R$_6$ are as previously defined; and
  (8) R$_1$ and R$_2$ taken together are=O;

R$_3$ is selected from the group consisting of:
  (1) hydrogen;
  (2) a hydroxy protecting group;
  (3) —C(O)—(C$_1$–C$_{12}$-alkyl), optionally substituted with one or more substituents selected from the group consisting of: halogen, aryl, substituted aryl, heterocyclic, substituted heterocyclic, —OR$_5$ and —NR$_5$R$_6$, where R$_5$ and R$_6$ are as previously defined;
  (4) C$_1$–C$_6$-alkyl, optionally substituted with one or more substituents selected from the group consisting of: halogen, aryl, substituted aryl, heterocyclic, substituted heterocyclic, —OR$_5$ and —NR$_5$R$_6$, where R$_5$ and R$_6$ are as previously defined;
  (5) C$_2$–C$_6$-alkenyl, optionally substituted with one or more substituents selected from the group consisting of: halogen, aryl, substituted aryl, heterocyclic, substituted heterocyclic, —OR$_5$ and —NR$_5$R$_6$, where R$_5$ and R$_6$ are as previously defined; and
  (6) C$_2$–C$_6$-alkynyl, optionally substituted with one or more substituents selected from the group consisting of: halogen, aryl, substituted aryl, heterocyclic, substituted heterocyclic, —OR$_5$ and —NR$_5$R$_6$, where R$_5$ and R$_6$ are as previously defined;

R$_4$ is —M—Y, where M and Y are as previously defined; and

R$^P$ is hydrogen or a hydroxy protecting group.

In another embodiment, the present invention provides processes for preparing novel compounds represented by Formula I wherein the groups A, B, R$_1$, R$_2$, R$_3$, R$_4$, R$_5$, R$_6$, R$_7$, R$_8$, R$_9$, R$_{10}$, R$_{11}$, M, Y, W and R$^P$ are as previously defined.

DETAILED DESCRIPTION OF THE INVENTION

The present invention relates to compounds represented by Formula I as described above.

Representative compounds of the invention include the following:

Compound of Formula I: A=—CHO, B=—CH$_2$—N(CH$_3$)$_2$, R$_1$ and R$_2$ taken together are=O, R$_3$=H, R$_4$=H and R$^P$=H;

Compound of Formula I: A=—CHO, B=—CH$_2$—NH—CH$_2$CH$_2$Phenyl, R$_1$ and R$_2$ taken together are=O, R$_3$=H, R$_4$=H and R$^P$=H;

Compound of Formula I: A=—CHO, B=—CH$_2$—N(CH$_3$)—CH$_2$CH$_2$Phenyl, R$_1$ and R$_2$ taken together are=O, R$_3$=H, R$_4$=H and R$^P$=H;

Compound of Formula I: A=—CHO, B=—CH$_2$—NH—CH$_2$CH$_2$-(2-pyridyl) R$_1$ and R$_2$ taken together are=O, R$_3$=H, R$_4$=H and R$^P$=H;

Compound of Formula I: A=—CHO, B=—CH$_2$-4-morpholyl, R$_1$ and R$_2$ taken together are=O, R$_3$=H, R$_4$=H and R$^P$=H;

Compound of Formula I: A=—CHO, B=—CH$_2$-1-imidazolyl, R$_1$ and R$_2$ taken together are=O, R$_3$=H, R$_4$=H and R$^P$=H;

Compound of Formula I: A=—CHO, B=—CH$_2$—N(CH$_3$)$_2$, R$_1$ and R$_2$ taken together are=O, R$_3$=H, R$_4$=CH$_2$CHCH-(3-quinolyl) and R$^P$=H;

Compound of Formula I: A=CHO, B=morpholyl, R$_1$ and R$_2$ taken together are=O, R$_3$=H, R$_4$=CH$_2$CC-(3-quinolyl) and R$^P$=H;

Compound of Formula I: A=CHO, B=morpholyl, R$_1$ and R$_2$ taken together are=O, R$_3$=H R$_4$=CH$_2$CHCH-(3-quinolyl) and R$^P$=H;

Compound of Formula I: A=CHO, B=morpholyl, R$_1$ and R$_2$ taken together are=O, R$_3$=H, R$_4$=CH$_2$CH$_2$CH$_2$-(3-quinolyl) and R$^P$=H;

Compound of Formula I: A=CHO, B=morpholyl, R$_1$ and R$_2$ taken together are=O, R$_3$=H, R$_4$=CH$_2$CC-(5-pyrimidyl) and R$^P$=H;

Compound of Formula I: A=CHO, B=morpholyl, R$_1$ and R$_2$ taken together are=O, R$_3$=H, R$_4$=CH$_2$CHCH-(5-pyrimidyl) and R$^P$=H;

Compound of Formula I: A=CHO, B=morpholyl, R$_1$ and R$_2$ taken together are=O, R$_3$=H, R$_4$=CH$_2$CH$_2$CH$_2$-(5-pyrimidyl) and R$^P$=H;

Compound of Formula I: A=CHO, B=morpholyl, R$_1$ and R$_2$ taken together are=O, R$_3$=H, R$_4$=CH$_2$CCCH$_2$-(phenyl) and R$^P$=H;

Compound of Formula I: A=CHO, B=morpholyl, R$_1$ and R$_2$ taken together are=O, R$_3$=H, R$_4$=CH$_2$CHCHCH$_2$-(phenyl) and R$^P$=H;

Compound of Formula I: A=CHO, B=morpholyl, R$_1$ and R$_2$ taken together are=O, R$_3$=H, R$_4$=CH$_2$CH$_2$CH$_2$CH$_2$-(phenyl) and R$^P$=H;

Compound of Formula I: A=CHO, B=morpholyl, R$_1$ and R$_2$ taken together are=O, R$_3$=H, R$_4$=CH$_2$CCCH$_2$-(4-fluorophenyl) and R$^P$=H;

Compound of Formula I: A=CHO, B=morpholyl, R$_1$ and R$_2$ taken together are=O, R$_3$=H, R$_4$=CH$_2$CHCHCH$_2$-(4-fluorophenyl) and R$^P$=H;

Compound of Formula I: A=CHO, B=morpholyl, R$_1$ and R$_2$ taken together are=O, R$_3$=H, R$_4$=CH$_2$CH$_2$CH$_2$CH$_2$-(4-fluorophenyl) and R$^P$=H;

Compound of Formula I: A=CHO, B=morpholyl, R$_1$ and R$_2$ taken together are=O, R$_3$=H, R$_4$=CH$_2$CCCH$_2$-(3-quinolyl) and R$^P$=H;

Compound of Formula I: A=CHO, B=morpholyl, R$_1$ and R$_2$ taken together are=O, R$_3$=H, R$_4$=CH$_2$CHCHCH$_2$-(3-quinolyl) and R$^P$=H;

Compound of Formula I: A=CHO, B=morpholyl, R$_1$ and R$_2$ taken together are=O, R$_3$=H, R$_4$=CH$_2$CH$_2$CH$_2$CH$_2$-(3-quinolyl) and R$^P$=H;

Compound of Formula I: A=CHO, B=morpholyl, R$_1$ and R$_2$ taken together are=O, R$_3$=H, R$_4$=CH$_2$CC-(2-pyridyl) and R$^P$=H;

Compound of Formula I: A=CHO, B=morpholyl, R$_1$ and R$_2$ taken together are=O, R$_3$=H, R$_4$=CH$_2$CHCH-(2-pyridyl) and R$^P$=H;

Compound of Formula I: A=CHO, B=morpholyl, R$_1$ and R$_2$ taken together are=O, R$_3$=H, R$_4$=CH$_2$CH$_2$CH$_2$-(2-pyridyl) and R$^P$=H;

Compound of Formula I: A=CHO, B=morpholyl, R$_1$ and R$_2$ taken together are=O, R$_3$=H, R$_4$=CH$_2$CC-(3-pyridyl) and R$^P$=H;

Compound of Formula I: A=CHO, B=morpholyl, R$_1$ and R$_2$ taken together are=O, R$_3$=H, R$_4$=CH$_2$CHCH-(3-pyridyl) and R$^P$=H;

Compound of Formula I: A=CHO, B=morpholyl, R$_1$ and R$_2$ taken together are=O, R$_3$=H, R$_4$=CH$_2$CH$_2$CH$_2$-(3-pyridyl) and R$^P$=H;

Compound of Formula I: A=CHO, B=CH$_2$F, R$_1$ and R$_2$ taken together are=O, R$_3$=H, R$_4$=CH$_2$CC-(3-quinolyl) and R$^P$=H;

Compound of Formula I: A=CHO, B=CH$_2$F, R$_1$ and R$_2$ taken together are=O, R$_3$=H, R$_4$=CH$_2$CHCH-(3-quinolyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$-(3-quinolyl) and R$^P$=H;

Compound of Formula I: A=CHO, B=CH$_2$F, R$_1$ and R$_2$ taken together are=O, R$_3$=H, R$_4$=CH$_2$CC-(5-pyrimidyl) and R$^P$=H;

Compound of Formula I: A=CHO, B=CH$_2$F, R$_1$ and R$_2$ taken together are=O, R$_3$=H, R$_4$=CH$_2$CHCH-(5-pyrimidyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$-(5-pyrimidyl) and R$^P$=H;

Compound of Formula I: A=CHO, B=CH$_2$F, R$_1$ and R$_2$ taken together are=O, R$_3$=H, R$_4$=CH$_2$CCCH$_2$-(phenyl) and R$^P$=H;

Compound of Formula I: A=CHO, B=CH$_2$F, R$_1$ and R$_2$ taken together are=O, R$_3$=H, R$_4$=CH$_2$CHCHCH$_2$-(phenyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$CH$_2$-(phenyl) and R$^P$=H;

Compound of Formula I: A=CHO, B=CH$_2$F, R$_1$ and R$_2$ taken together are=O, R$_3$=H, R$_4$=CH$_2$CCCH$_2$-(4-fluorophenyl) and R$^P$=H;

Compound of Formula I: A=CHO, B=CH$_2$F, R$_1$ and R$_2$ taken together are=O, R$_3$=H, R$_4$=CH$_2$CHCHCH$_2$-(4-fluorophenyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$CH$_2$-(4-fluorophenyl) and R$^P$=H;

Compound of Formula I: A=CHO, B=CH$_2$F, R$_1$ and R$_2$ taken together are=O, R$_3$=H, R$_4$=CH$_2$CCCH$_2$-(3-quinolyl) and R$^P$=H;

Compound of Formula I: A=CHO, B=CH$_2$F, R$_1$ and R$_2$ taken together are=O, R$_3$=H, R$_4$=CH$_2$CHCHCH$_2$-(3-quinolyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$CH$_2$-(3-quinolyl) and R$^P$=H;

Compound of Formula I: A=CHO, B=CH$_2$F, R$_1$ and R$_2$ taken together are=O, R$_3$=H, R$_4$=CH$_2$CC-(2-pyridyl) and R$^P$=H;

Compound of Formula I: A=CHO, B=CH$_2$F, R$_1$ and R$_2$ taken together are=O, R$_3$=H, R$_4$=CH$_2$CHCH-(2-pyridyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$-(2-pyridyl) and R$^P$=H;

Compound of Formula I: A=CHO, B=CH$_2$F, R$_1$ and R$_2$ taken together are=O, R$_3$=H, R$_4$=CH$_2$CC-(3-pyridyl) and R$^P$=H;

Compound of Formula I: A=CHO, B=CH$_2$F, R$_1$ and R$_2$ taken together are=O, R$_3$=H, R$_4$=CH$_2$CHCH-(3-pyridyl) and R$^P$=H;

Compound of Formula I: A=CHO, B=CH$_2$F, R$_1$ and R$_2$ taken together are=O, R$_3$=H, R$_4$=CH$_2$CH$_2$CH$_2$-(3-pyridyl) and R$^P$=H;

Compound of Formula I: A=CHO, B=CN, R$_1$ and R$_2$ taken together are=O, R$_3$=H, R$_4$=CH$_2$CC-(3-quinolyl) and R$^P$=H;

Compound of Formula I: A=CHO, B=CN, R$_1$ and R$_2$ taken together are=O, R$_3$=H, R$_4$=CH$_2$CHCH-(3-quinolyl) and R$^P$=H;

Compound of Formula I: A=CHO, B=CN, R$_1$ and R$_2$ taken together are=O, R$_3$=H, R$_4$=CH$_2$CH$_2$CH$_2$-(3-quinolyl) and R$^P$=H;

Compound of Formula I: A=CHO, B=CN, R$_1$ and R$_2$ taken together are=O, R$_3$=H, R$_4$=CH$_2$CC-(5-pyrimidyl) and R$^P$=H;

Compound of Formula I: A=CHO, B=CN, R$_1$ and R$_2$ taken together are=O, R$_3$=H, R$_4$=CH$_2$CHCH-(5-pyrimidyl) and R$^P$=H;

Compound of Formula I: A=CHO, B=CN, R$_1$ and R$_2$ taken together are=O, R$_3$=H, R$_4$=CH$_2$CH$_2$CH$_2$-(5-pyrimidyl) and R$^P$=H;

Compound of Formula I: A=CHO, B=CN, R$_1$ and R$_2$ taken together are=O, R$_3$=H, R$_4$=CH$_2$CCCH$_2$-(phenyl) and R$^P$=H;

Compound of Formula I: A=CHO, B=CN, R$_1$ and R$_2$ taken together are=O, R$_3$=H, R$_4$ CH$_2$CHCHCH$_2$-(phenyl) and R$^P$=H;

Compound of Formula I: A=CHO, B=CN, R$_1$ and R$_2$ taken together are=O, R$_3$=H, R$_4$=CH$_2$CH$_2$CH$_2$CH$_2$-(phenyl) and R$^P$=H;

Compound of Formula I: A=CHO, B=CN, R$_1$ and R$_2$ taken together are=O, R$_3$=H, R$_4$=CH$_2$CCCH$_2$-(4-fluorophenyl) and R$^P$=H;

Compound of Formula I: A=CHO, B=CN, R$_1$ and R$_2$ taken together are=O, R$_3$=H, R$_4$=CH$_2$CHCHCH$_2$-(4-fluorophenyl) and R$^P$=H;

Compound of Formula I: A=CHO, B=CN, R$_1$ and R$_2$ taken together are=O, R$_3$=H, R$_4$=CH$_2$CH$_2$CH$_2$CH$_2$-(4-fluorophenyl) and R$^P$=H;

Compound of Formula I: A=CHO, B=CN, R$_1$ and R$_2$ taken together are=O, R$_3$=H, R$_4$=CH$_2$CCCH$_2$-(3-quinolyl) and R$^P$=H;

Compound of Formula I: A=CHO, B=CN, R$_1$ and R$_2$ taken together are=O, R$_3$=H, R$_4$=CH$_2$CHCHCH$_2$-(3-quinolyl) and R$^P$=H;

Compound of Formula I: A=CHO, B=CN, R$_1$ and R$_2$ taken together are=O, R$_3$=H, R$_4$=CH$_2$CH$_2$CH$_2$CH$_2$-(3-quinolyl) and R$^P$=H;

Compound of Formula I: A=CHO, B=CN, R$_1$ and R$_2$ taken together are=O, R$_3$=H, R$_4$=CH$_2$CC-(2-pyridyl) and R$^P$=H;

Compound of Formula I: A=CHO, B=CN, R$_1$ and R$_2$ taken together are=O, R$_3$=H, R$_4$=CH$_2$CHCH-(2-pyrdiyl) and R$^P$=H;

Compound of Formula I: A=CHO, B=CN, R$_1$ and R$_2$ taken together are=O, R$_3$=H, R$_4$=CH$_2$CH$_2$CH$_2$-(2-pyridyl) and R$^P$=H;

Compound of Formula I: A=CHO, B=CN, R$_1$ and R$_2$ taken together are=O, R$_3$=H, R$_4$=CH$_2$CC-(3-pyridyl) and R$^P$=H;

Compound of Formula I: A=CHO, B=CN, R$_1$ and R$_2$ taken together are=O, R$_3$=H, R$_4$=CH$_2$CHCH-(3-pyridyl) and R$^P$=H; and Compound of Formula I: A=CHO, B=CN, R$_1$ and R$_2$ taken together are=O, R$_3$=H, R$_4$=CH$_2$CH$_2$CH$_2$-(3-pyridyl) and R$^P$=H.

Definitions

The terms "C$_1$–C$_3$-alkyl," "C$_1$–C$_6$-alkyl" or "C$_1$–C$_{12}$-alkyl," as used herein, saturated, straight- or branched-chain hydrocarbon radicals containing between one and three, one and six or one and twelve carbon atoms, respectively. Examples of C$_1$–C$_3$ alkyl radicals include, but are not limited to, methyl, ethyl, propyl and isopropyl, and examples of C$_1$–C$_6$-alkyl radicals include, but are not limited to, methyl, ethyl, propyl, isopropyl, n-butyl, tert-butyl, neopentyl and n-hexyl, and examples of C$_1$–C$_{12}$-alkyl radicals include, but are not limited to, methyl, ethyl, propyl, isopropyl, n-butyl, tert-butyl, neopentyl, n-hexyl, n-octyl, n-decyl, and n-dodecyl.

The term "C$_2$–C$_6$-alkenyl," as used herein, refers to straight- or branched-chain hydrocarbon radicals containing between two and six carbon atoms with one or more double bonds in the chain. Examples of C$_2$–C$_6$-alkenyl include, but are not limited to, propenyl, isobutenyl, 1,3-hexadienyl, n-hexenyl, and 3-pentenyl.

The term "C$_2$–C$_6$-alkynyl," as used herein, refers to straight- or branched-chain hydrocarbon radicals containing between two and six carbon atoms with one or more triple bonds in the chain optionally containing one or more double bond. Examples of C$_2$–C$_6$-alkynyl include, but are not limited to, propynyl, isopentynyl, 1,3-hexadiynyl, n-hexynyl, 3-pentynyl, and 1-hexen-3-ynyl.

The term "C$_1$–C$_6$-alkoxy," as used herein, refers to a C$_1$–C$_6$-alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, tert-butoxy, neopentoxy and n-hexoxy.

The term "C$_1$–C$_3$-alkyl-amino," as used herein, refers to one or two C$_1$–C$_3$-alkyl groups, as previously defined, attached to the parent molecular moiety through a nitrogen atom. Examples of C$_1$–C$_3$-alkyl-amino include, but are not limited to, methylamino, dimethylamino, ethylamino, diethylamino, and propylamino.

The term "aprotic solvent," as used herein, refers to a solvent that is relatively inert to proton activity, i.e., not acting as a proton-donor. Examples include, but are not limited to, hydrocarbons such as, for example, hexane and toluene, and the like, halogenated hydrocarbons such as, for example, methylene chloride, ethylene chloride, chloroform, and the like, heterocyclic compounds such as, for example, tetrahydrofuran, N-methyl pyrrolidinone, and the like, and ethers such as, for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the Techniques of Chemistry Series, John Wiley & Sons, NY, 1986.

The term "aryl," as used herein, refers to unsubstituted carbocyclic aromatic groups including, but not limited to, phenyl, 1- or 2-naphthyl and the like.

The terms "$C_3$–$C_5$-cycloalkyl- and $C_3$–$C_7$-cycloalkyl," as used herein, refer to carbocyclic groups of 3 to 5 or 3 to 7 carbon atoms, respectively, such as for example, cyclopropyl, cyclobutyl, cyclopentyl, cyclohexyl, and cycloheptyl.

The term "$C_1$–$C_3$-alkyl-$C_3$–$C_5$-cycloalkyl," as used herein refers to a $C_3$–$C_5$-cycloalkyl radical, as defined above, attached to a $C_1$–$C_3$-alkyl radical by replacement of a hydrogen atom on the latter.

The terms "halo" and "halogen," as used herein, refer to an atom selected from fluorine, chlorine, bromine and iodine.

The term "heteroaryl," as used herein, refers to a cyclic aromatic radical having from five to ten ring atoms of which one ring atom is selected from S, O and N; zero, one or more ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic," as used herein, refers to heterocycloalkyl and heteroaryl. The term "substituted heterocyclic," as used herein, refers to substituted heterocycloalkyl and substituted heteroaryl.

The term "substituted aryl," as used herein refers to an aryl group, as defined herein, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_7$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl," as used herein refers to a heteroaryl group as defined herein substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heterocycloalkyl," as used herein, refers to a heterocycloalkyl group, as defined above, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted cycloalkyl," as used herein refers to a $C_3$–$C_7$ cycloalkykl group, as defined above, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_2$–$C_6$-alkyl, $SO_2$-aryl, $SO_2$- heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, amino, benzylamino, arylamino, heteroarylamino, $C_1$–$C_3$-alkyl-amino, thio, arylthio, heteroarylthio, benzyl-thio, $C_1$–$C_6$-alkyl-thio, or methylthiomethyl.

"Hydroxy-protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, *Protective Groups in Organic Synthesis,* 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy," refers to a hydroxy group protected with a hydroxy protecting group, as defined above, including, for example, but not limited to, benzoyl, acetyl, trimethylsilyl, triethylsilyl, methoxymethyl groups.

"Aldehyde-protecting group," as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G. M. Wuts, *Protective Groups in Organic Synthesis,* op. cit. Examples of aldehyde-protecting groups include, but are not limited to, acetals, ketals, O-substituted cyanohydrins, substituted hydrazones, imines and the like.

The term "protected aldehyde" refers to an aldehyde group protected with an aldehyde protecting group, as defined above, including, for example, but not limited to, dimethyl acetyl, 1,3-dioxolane, 1,3-dioxane and the like.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of protogenic solvents may be found in organic chemistry textbooks or in specialized monographs, for example: *Organic Solvents Physical Properties and Methods of Purification,* 4th ed., edited by John A. Riddick et al., op. cit.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems,* Vol. 14 of the A.C.S. Symposium Series and in Edward B. Roche, ed., *Bioreversible Carriers in Drug*

*Design*, American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 $\mu$l/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 g/ml.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other animal in single or in divided doses can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of the compounds of the present invention per day in single or multiple doses.

The pharmaceutical compositions of this invention can be administered to fish by blending them in the fish feed to be administered orally or may be dissolved in water in which sick fish are placed to swim around (a method using a so-called "medicated bath"). The dosage for the treatment of fish differs depending upon the purpose of administration (prevention or cure of disease) and type, size and extent of infection of the fish to be treated. Generally, a dosage of 5–1000 mg, preferably 20–100 mg, per kg of body weight of fish may be administered per day, either at one time or divided into several times. It will be recognized that the above specified dosage is only a general range which may be reduced or increased depending on the age, body weight, condition of disease, etc. of the fish.

Abbreviations

Abbreviations which have been used in the descriptions of the scheme and the examples that follow are: AIBN for azobisisobutyronitrile; BOC for tert-butoxycarbonyl; Bu$_3$SnH for tributyltin hydride; BSA for bis(trimethylsilyl) acetamide; CDI for carbonyldiimidazole; DBU for 1,8-diazabicyclo[5.4.0]undec-7-ene; DCC for 1,3-dicyclohexylcarbodiimide; DEAD for diethylazodicarboxylate; DIC for 2-chloro-N,N-dimethylpropylamine, hydrochloride, DIEA for diisopropylethylamine; DMF for dimethyl formamide; DMSO for dimethyl sulfoxide; DPPA for diphenylphosphoryl azide; EtOAc for ethyl acetate; HMDS for 1,1,1,3,3,3-hexamethyldisilazane; MeOH for methanol; NaN(TMS)$_2$ for sodium bis(trimethylsilyl)amide; NMO for N-methylmorpholine N-oxide; PCC for pyridinium chlorochromate; PDC for pyridinium dichromate; TEA for triethylamine; THF for tetrahydrofuran; TPP for triphenylphosphine; DMAP for 4-N,N-dimethylamino pyridine; TFA for trifluoroacetic acid; KHMDS for potassium bis(trimethylsilyl)amide; Ac for acetyl; Bz for benzoyl; TBAF for tetrabutyl ammonium fluoride; m-CPBA for meta-chloro perbenzoic acid; TBDMSCl for tert-butyl dimethyl silyl chloride; TES for triethylsilyl; TMS for trimethylsilyl and TBDPSCl for tert-butyldiphenyl silyl chloride.

Synthetic Methods

The compounds and processes of the present invention will be better understood in connection with the following synthetic schemes which are illustrative of the methods by which the compounds of the invention may be prepared. The groups A, $R_1$, $R_2$, $R_3$, $R_4$, $R_5$, $R_6$, $R_7$, $R_8$ and $R^P$ are as defined previously unless otherwise noted below. The groups $R^P_1$, $R^P_2$, $R^P_3$ and $R^P_4$ are hydroxy-protecting groups and the groups R' and R" are $C_1$–$C_6$-alkyl or taken together are —CH$_2$CH$_2$— or —CH$_2$CH$_2$CH$_2$—.

Scheme 1
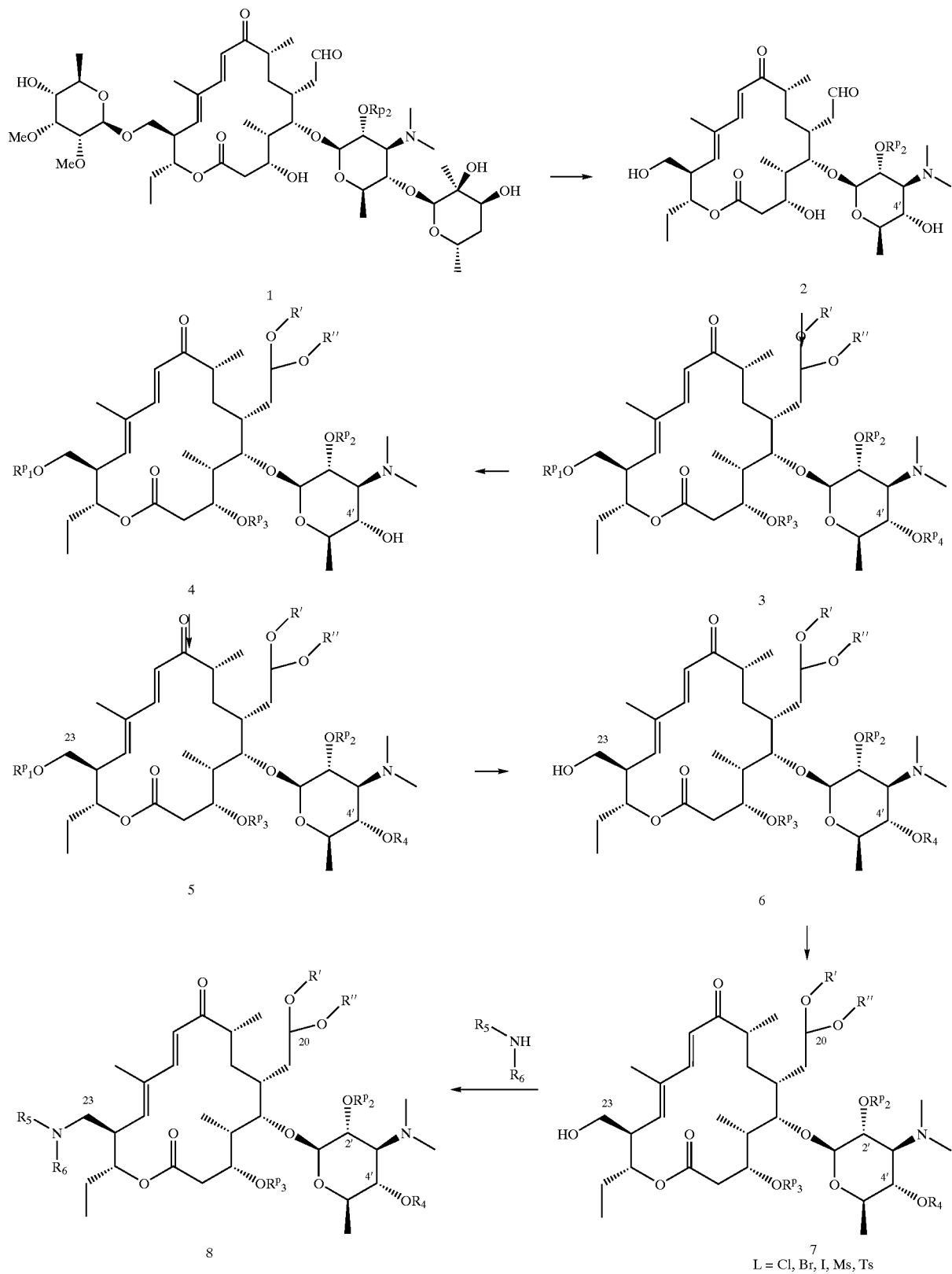

One synthetic method of the present invention pertains to the preparation of the compounds of Formula I by treating 2'-protected tylosin (1 of Scheme 1) with a dilute aqueous acid (0.1–5 N), such as hydrochloric acid, sulfuric acid, p-toluenesulfonic acid, trifluoroacetic acid, acetic acid, or the like or combinations thereof, optionally in an organic solvent such as acetone, acetonitrile, methanol, ethanol or the like, or combinations thereof, at a temperature from about 0° C. to about 100° C. for about 1 to 24 hours, to provide protected 2, where $R^P{}_2$ is an ester. 2 is treated with acetyl chloride, hydrochloric acid, acetic acid, or the like, to provide a solution of pH from about 1 to about 4 in an alcoholic solvent, such as methanol, ethanol, ethylene glycol, or the like, to provide an acetal intermediate. The acetal intermediate is further treated with a silylating agent, such as HMDS, BSA, triethylsilyl chloride, TBDMSCl, TBDPSCl, or the like, optionally with the addition of a catalyst, such as DMAP, imidazole or the like, in an aprotic solvent such as methylene chloride, ethylene chloride, THF, chloroform, DMF, acetonitrile, or the like, at a temperature from about 0° C. to about 50° C. for about 1 to 48 hours to provide 3. Selective deprotection at the 4'-position in 3 is achieved by treating 3 with an acid such as formic acid, acetic acid, propanoic acid, phenolic acid, or the like, in an organic solvent such acetone, acetonitrile, methanol, ethanol, or the like or combinations thereof, at a temperature from about 0° C. to about 50° C. for about 1 to 24 hours to provide 4. 4 is reacted with an alkylating agent, such as an alkyl halide, alkyl sulphonate, propargyl halide, allyl halide, arylallyl halide, heteroarylallyl halide, benzyl halide, or the like, in the presence of a base, such as sodium hydride, potassium hydride, potassium tert-butoxide, potassium hydroxide, KHMDS, or the like, in an aprotic solvent such as THF, DMSO, DMF, dioxane, or the like or mixtures thereof, at a temperature from about –20° C. to about 60° C. to provide 5. Further selective deprotection of the siloxyl group at the C-23 position in 5 can be effected by treatment with an acid, such as acetic acid, propanoic acid, or the like, in an organic solvent, such as acetone, acetonitrile, methanol, ethanol, or the like or combinations thereof, at a temperature from about room temperture to about 100° C. for about 1 to 48 hours to provide 6. 6 can be further derivatized to 7, where L is a halide, such as chloride, bromide or iodide, by treating with triphenylphosphine and a halogenating agent, such as chlorine, bromine, iodine, carbon tetrachloride, carbon tetrabromide, carbon tetraiodide or the like, in an aprotic organic solvent, such as methylene chloride, ethylene chloride, THF, chloroform, DMF, acetonitrile, or the like, at a temperature from about –78° C. to about 50° C. for about 30 minutes to 48 hours. 7, where L is a sulfonate such as mesylate (Ms) or tosylate (Ts), can be prepared by treating 6 with the corresponding sulfonic anhydride, sulfonyl chloride or mixed anhydride in an aprotic organic solvent such as methylene chloride, ethylene chloride, THF, chloroform or the like at a temperature from about –78° C. to about 50° C. for about 30 minutes to 48 hours in the presence of an amine base, such as pyridine, diethylamine, triethylamine or the like, optionally by adding a catalyst such as DMAP, imidazole or the like. 8 is obtained by treating 7 with the corresponding amine (for example, $NHR_5R_6$) in a solvent such as water, ethanol, THF, DMF, DMSO, 1,4-dioxane, or the like, or combinations thereof, at a temperature from about 0° C. to about 100° C. for about 1 to 24 hours. Deprotection at the C-20 acetal and C-3 siloxyl group in 7 and 8 can be carried out in one step by treating with an aqueous acid, such as sulfuric acid, hydrochloric acid, hydrofluoric acid, acetic acid or the like in an organic solvent, such as acetone, acetonitrile, THF, DMF, DMSO, 1,4-dioxane, or the like, or combinations thereof, at a temperature from about 0° C. to about 100° C. for about 1 to 24 hours, to provide a 2'-protected intermediate. Further removal of the $R^P{}_2$ protecting group at the 2'-position, where $R^P{}_2$ is an ester, can be done by stirring in methanol at a temperature from about room temperature to about reflux temperature to provide compounds of Formula I.

Scheme 2

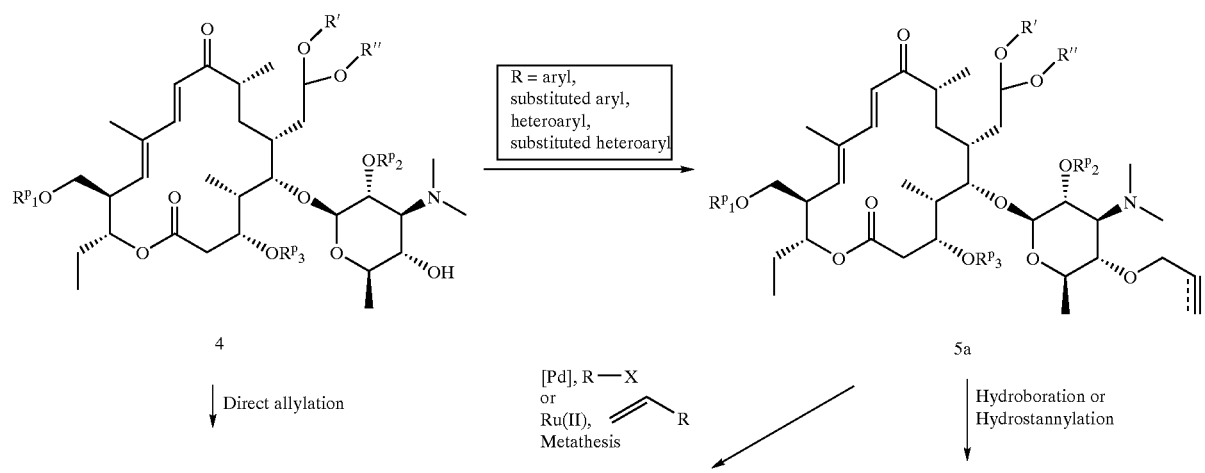

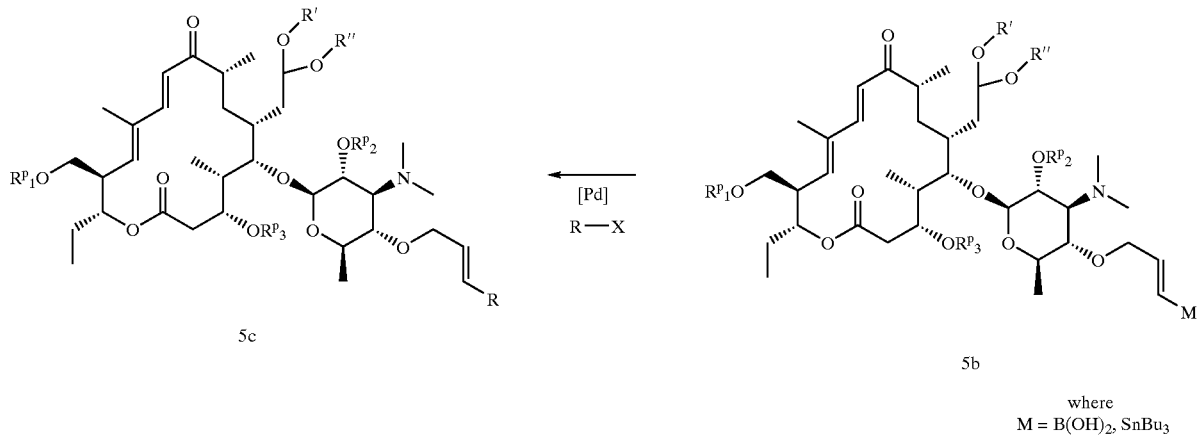

where
M = B(OH)$_2$, SnBu$_3$

Another synthetic method of the present invention pertaining to the preparation of compounds of Formula I is illustrated in Scheme 2. 5a of Scheme 2 is obtained by alkylating 4 with allyl bromide or propargyl bromide, as described in Scheme 1. The propargyl group of 5a is reduced with a variety of borane reagents, such as catecholborane, BH$_3$, thexylborane, or the like, to give the vinyl boronic acid derivative or stannane reagents, such as tributyltin hydride, to give vinyl stannane derivatives, to provide 5b. 5c is obtained by subjecting 5b to further palladium catalyzed Suzuki or Stille coupling reactions with R—X, where R is an aryl, heteroaryl, substituted aryl, or substituted heteroaryl group, and X is a halide or triflate (see (a) Suzuki, *Chemical Reviews*, 1995, 95, 2457; (b) Suzuki, *Pure & Appl. Chem.* 1991, 63, 419; (c) Reviews: Farina, V., Krishnamurthy, V., and Scott, W. J., *The Stille Reaction*, 1$^{st}$ ed.; Wiley, New York, 1998.). In addition, 5a is treated with R—X, where R is an aryl, heteroaryl, substituted aryl, or substituted heteroaryl group, and X is a halide or triflate, in the presence of a palladium catalyst [Pd(0) or Pd(II)] to provide 5c (see (a) Heck, *Palladium Reagents in Organic Synthesis*, Academic Press: New York, 1985, Chapter 1; (b) Sonogashira, *Comprehensive Organic Synthesis*, Volume 3, Chapters 2,4; (c) Sonogashira, *Synthesis* 1977, 777). Under the Heck coupling conditions, regioisomers and stereoisomers of the double bond are possible. Alternatively, 5a can undergo a cross metathesis reaction with vinylaromatic derivatives, such as CH$_2$=CH—R, where R is an aryl, heteroaryl, substituted aryl, or substituted heteroaryl group, using ruthenium catalysts to provide 5c (see (a) *J. Org. Chem.* 2000, 65, 2204–2207; (b) Reviews: *Synlett.* 1999, 2, 267; (c) Reviews: Ivin, K. J.; Mol, J. C. *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Alternatively 4 of Scheme 2 is reacted with a tert-butyl allyl carbonate catalyzed by a palladium catalyst [Pd(0) or Pd(II)] to provide 5c directly (see (a) Trost, B. M. *Angew. Chem. Int. Ed. Eng.* 1989, 28, 1179. (b) Heck, Palladium Reagents in Organic Synthesis, Academic Press: New York, 1985, Chapter 1; and (c) Tsuji *Tetrahedron Lett.* 1992, 33, 2987). 5c is further transformed to compounds of formula I as described in Scheme 1 (such as for the transformation of 5 to 8).

Scheme 3

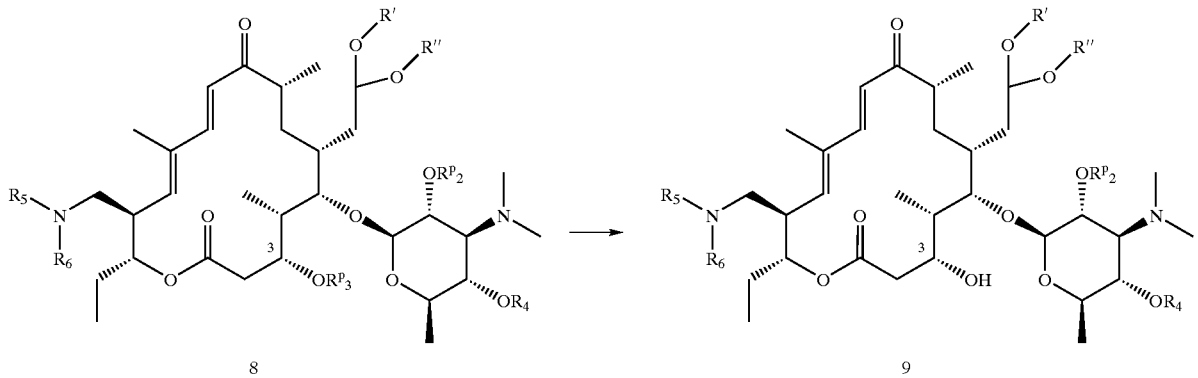

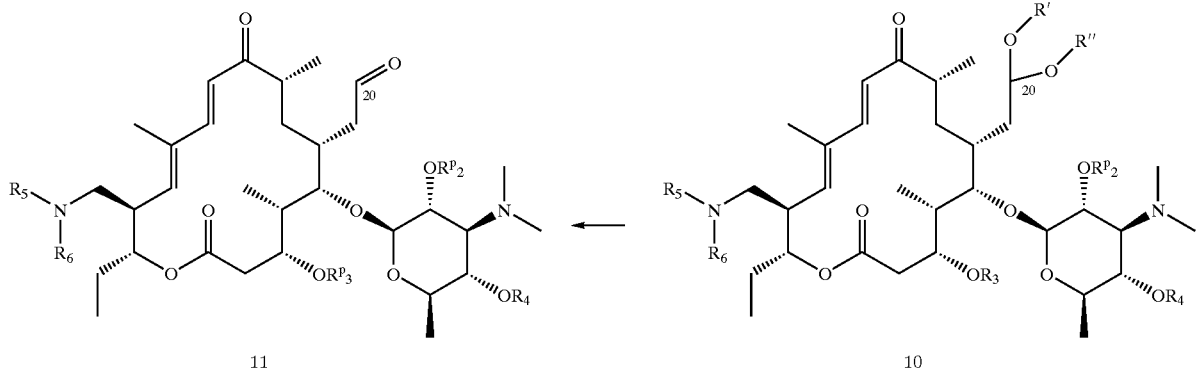

11 → 10

Yet another synthetic method of the present invention pertains to the preparation of the compounds of Formula I as illustrated in Scheme 3. 8 of scheme 3 is treated with TBAF or hydrofluoric acid to remove the C-3 silyl protecting group to provide 9. 9 is reacted with an alkylating agent, such as an alkyl halide, alkyl sulphonate, propargyl halide, allyl halide, arylallyl halide, heteroarylallyl halide, benzyl halide or the like, in the presence of a base, such as sodium hydride, potassium hydride, potassium tert-butoxide, potassium hydroxide, KHMDS, or the like, in an aprotic solvent such as, THF, DMSO, DMF, 1,4-dioxane, or the like, or mixtures thereof, at a temperature from about −20° C. to about 60° C., to provide 10. Deprotection of the C-20 acetal group can be effected by aqueous acidic solution, such as sulfuric acid, hydrochloric acid, hydrofluoric acid, acetic acid or the like, with optionally added organic solvent such as acetone, acetonitrile, THF, 1,4-dioxane or the like, or combinations thereof, at a temperature from about 0° C. to about 100° C. for 1–24 hours to provide a 2'-protected intermediate 11. Further removal of the $R^P{}_2$ protecting group at the 2'-position, where $R^P{}_2$ is an ester, can be done by stirring in methanol at a temperature from about room temperature to about reflux temperature, to provide compounds of Formula I.

Scheme 4

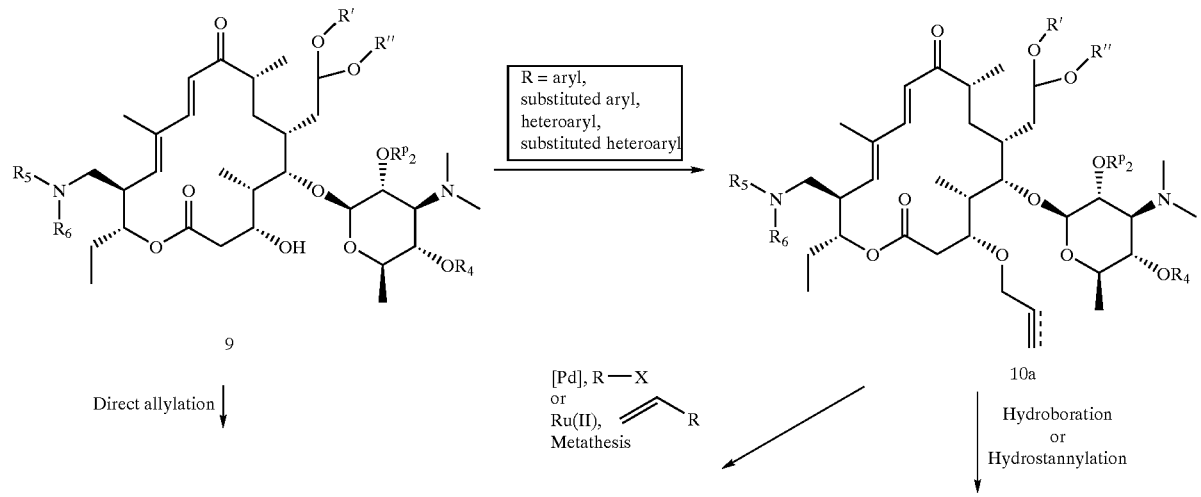

-continued

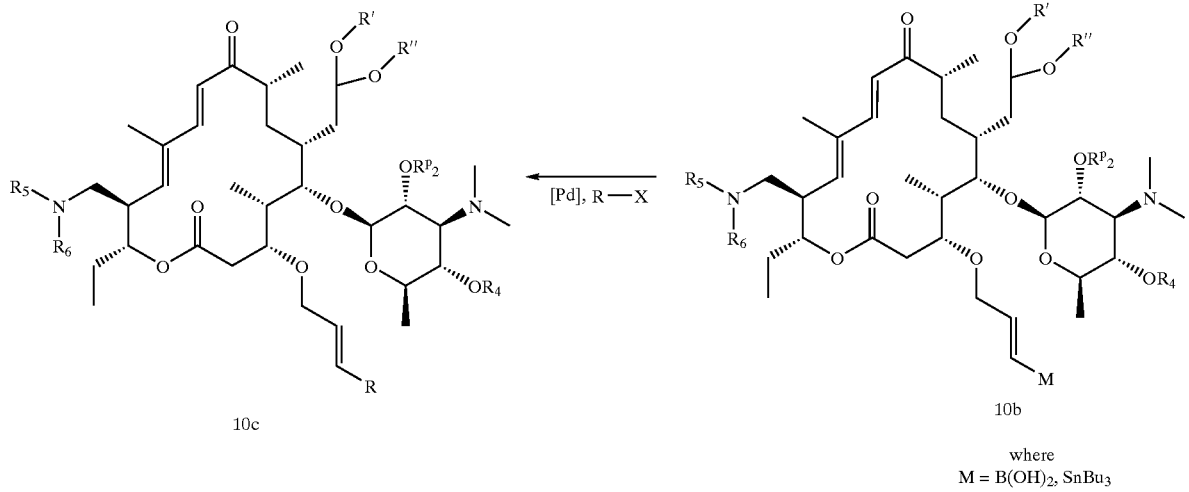

10c  ←  [Pd], R—X  10b where
M = B(OH)$_2$, SnBu$_3$

Another synthetic method of the invention pertains to the preparation of compounds of Formula I as illustrated in scheme 4. 10a in scheme 4 is obtained by alkylating 9 with allyl bromide or propargyl bromide, as described earlier in scheme 3. The propargyl group of 10a is reduced with a variety of borane reagents, such as catecholborane, BH$_3$, thexylborane, or the like, to give the vinyl boronic acid derivative or stannane reagents, such as tributyltin hydride, to give vinyl stannane derivatives 10b. 10c is obtained by subjecting 10b to further palladium catalyzed Suzuki or Stille coupling reactions with R—X, where R is an aryl, heteroaryl, substituted aryl, or substituted heteroaryl group, and X is a halide or triflate (see (a) Suzuki, Chemical Reviews, 1995, 95, 2457; (b) Suzuki, *Pure & Appl. Chem.* 1991, 63, 419; and (c) Reviews: Farina, V., Krishnamurthy, V., and Scott, W. J., *The Stille Reaction*, 1$^{st}$ ed.; Wiley, New York, 1998). In addition, 10a is treated with R—X, where R is an aryl, heteroaryl, substituted aryl, or substituted heteroaryl group, and X is a halide or triflate, in the presence of a palladium catalyst [Pd(0) or Pd(II)] to provide 10c (see (a) Heck, Palladium Reagents in Organic Synthesis, Academic Press: New York, 1985, Chapter 1; (b) Sonogashira, Comprehensive Organic Synthesis, Volume 3, Chapters 2 and 4; (c) Sonogashira, *Synthesis* 1977, 777). Under the Heck coupling conditions, regioisomers and stereoisomers of the double bond are possible. Alternatively, 10a can undergo a cross metathesis reaction with vinylaromatic derivatives, such as CH$_2$=CH—R, where R is an aryl, heteroaryl, substituted aryl, or substituted heteroaryl group, using ruthenium catalysts to provide 10c (see (a) *J. Org. Chem.* 2000, 65, 2204–2207; (b) Reviews: *Synlett.* 1999, 2, 267; (c) Reviews: Ivin, K. J., and Mol, J. C., *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; and (f) *Tetrahedron* 1998, 54, 4413–4450). Alternatively, 9 of scheme 4 is reacted with a tert-butyl allyl carbonate or tert-butyl arylallyl carbonate catalyzed by a palladium catalyst [Pd(0) or Pd(II)] to provide 10a or 10c directly (see (a) Trost, B. M. *Angew. Chem. Int. Ed. Eng.* 1989, 28, 1179; (b) Heck, Palladium Reagents in Organic Synthesis, Academic Press: New York, 1985, Chapter 1; (c) Tsuji *Tetrahedron Lett.* 1992, 33, 2987).

Scheme 5

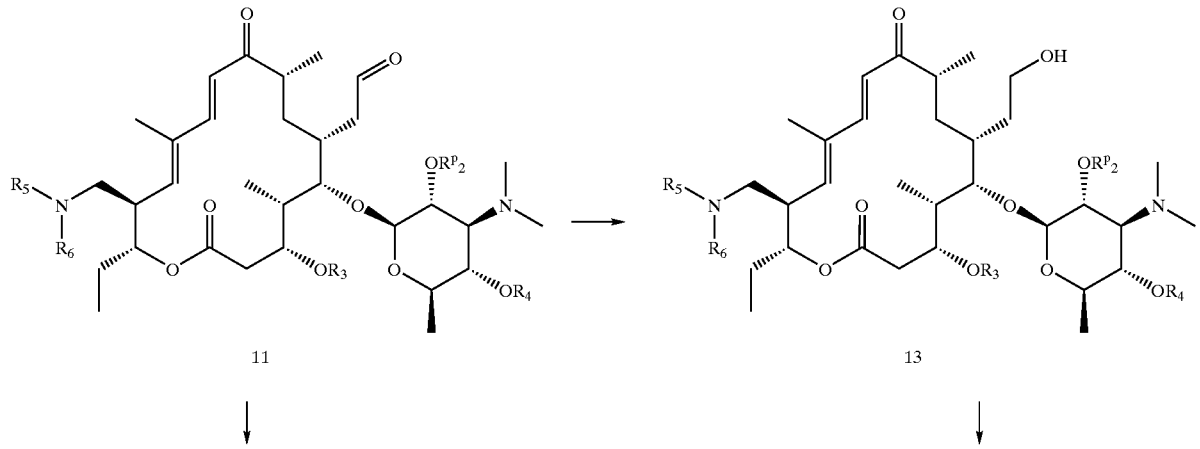

11 → 13

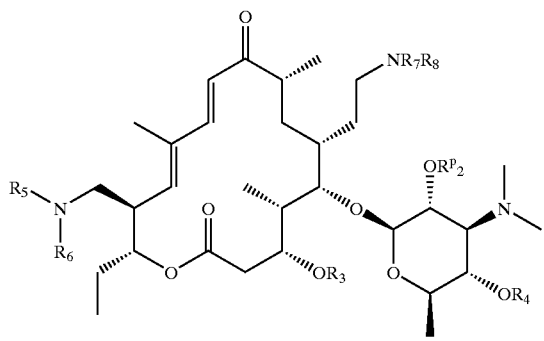

12

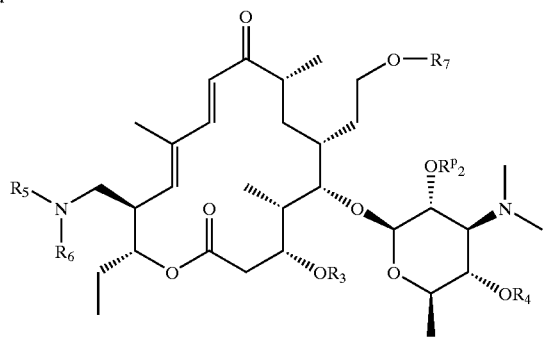

14

Scheme 5 illustrates yet another synthetic method of the present invention for the preparation of the compounds of Formula I. 11 in Scheme 5 can be derivatized to an amino derivative via reductive amination methods, for example, by treating with an amine compound in the presence of sodium borohydride, sodium cyanoborohydride, or the like, in an alcoholic solvent, such as methanol, ethanol or isopropanol or acetonitrile or the like, at a pH from about 2 to about 6, to provide 12. 11 can also be reduced to the corresponding alcohol with various hydride reducing agents, such as sodium borohydrides, lithium borohydrides, or the like, in an organic solvent such as methanol, ethanol, isopropanol, acetonitrile, THF, or the like, to provide 13. 13 can be converted to an ether compound of the invention by treatment with an alkyl halide, alkyl sulphonate, propargyl halide, allyl halide, arylallyl halide, heteroarylallyl halide, benzyl halide or the like, in the presence of a base, such as sodium hydride, potassium hydride, potassium tert-butoxide, potassium hydroxide, KHMDS, or the like, in an aprotic solvent, such as THF, DMSO, DMF, dioxane, or the like or mixtures thereof, at a temperature from about −20° C. to about 60° C. to provide 14. The $R^P_2$ protecting group at the 2'-position in 12, 13 and 14 can be removed by stirring in methanol at a temperature from about room temperature to about reflux temperature, where $OR^P_2$ is an ester, to provide compounds of Formula I.

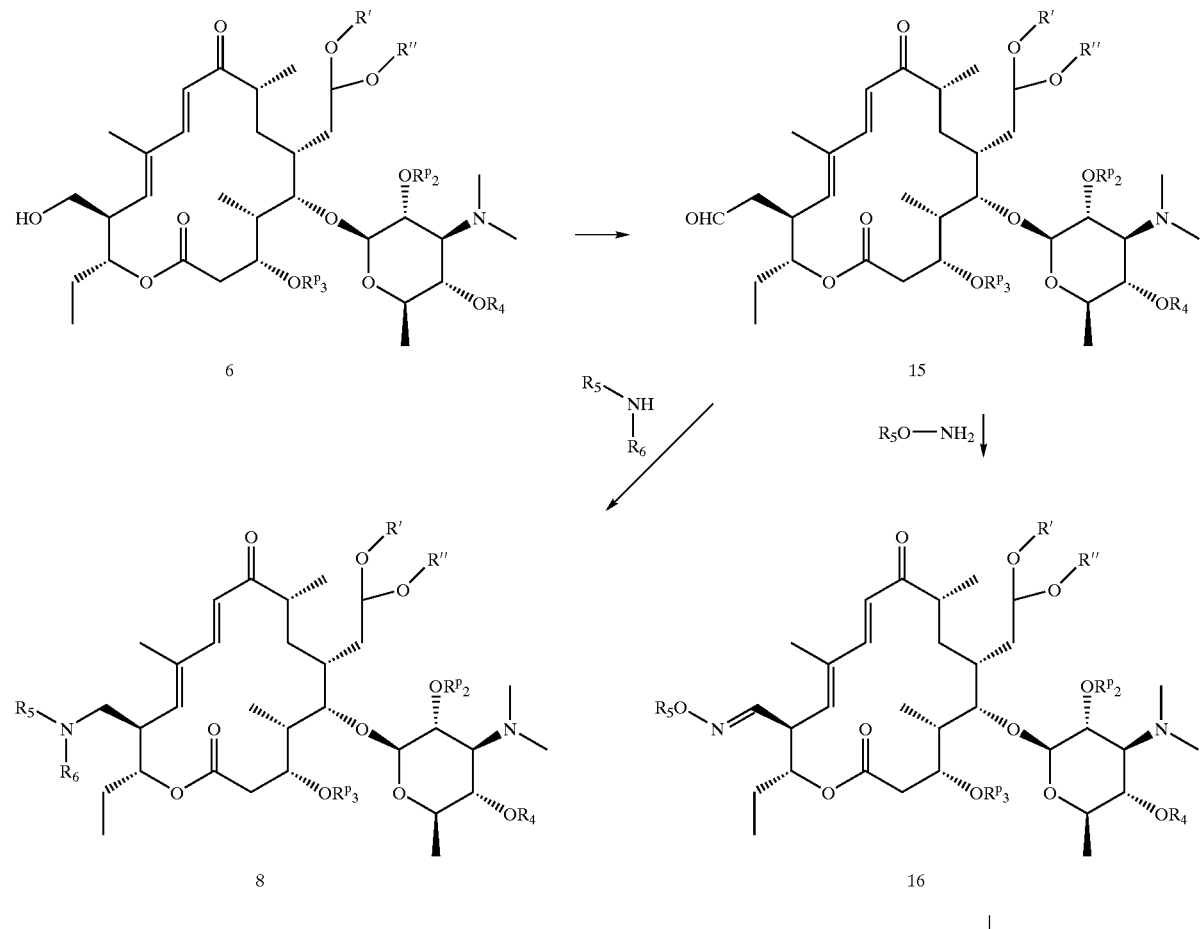

-continued

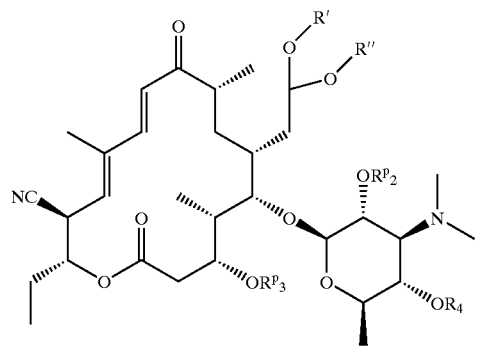

17

Another synthetic method of the present invention, Scheme 6, pertains to the preparation of compounds of Formula I. In Scheme 6, 6 is oxidized with an oxidant, such as PCC, PDC, chromium trioxide, or the like, or DMSO and the like, and an electrophilic reagent such as dicyclohexylcarbodiimide, trifluoroacetic anhydride, acetic anhydride, oxalyl chloride, sulfur trioxide, or the like, in an organic solvent such as methylene chloride, chloroform, ethylene chloride, or the like, at a temperature from about −45° C. to about 25° C. for about 1 to 48 hours, to provide 15. 15 is treated with an amine compound in the presence of sodium borohydride, sodium cyanoborohydride, or the like, in an alcoholic solvent such as methanol, ethanol or isopropanol or in acetonitrile, or the like, at a pH from about 2 to about 6, to provide 8. Treating 15 with a hydroxylamine of the general formula $R_5ONH_2$ where $R_5$ is as previously defined, in an alcoholic solvent such as methanol, ethanol or isopropanol, or in acetonitrile, optionally adding an acid catalyst such as acetic acid, hydrochloric acid, or the like, optionally with the addition of a base such as imidazole, DMAP, or the like, provides 16. 16, when $R_5$ is hydrogen, can be dehydrated by treating with DCC, DIC, or the like in an organic solvent such as methylene chloride, chloroform, dichloroethane, THF, or the like, and optionally adding cuprous chloride to give 17. 15, 16 and 17 can be further deprotected as previously described in Schemes 1–5 to provide compounds of Formula I.

Scheme 7

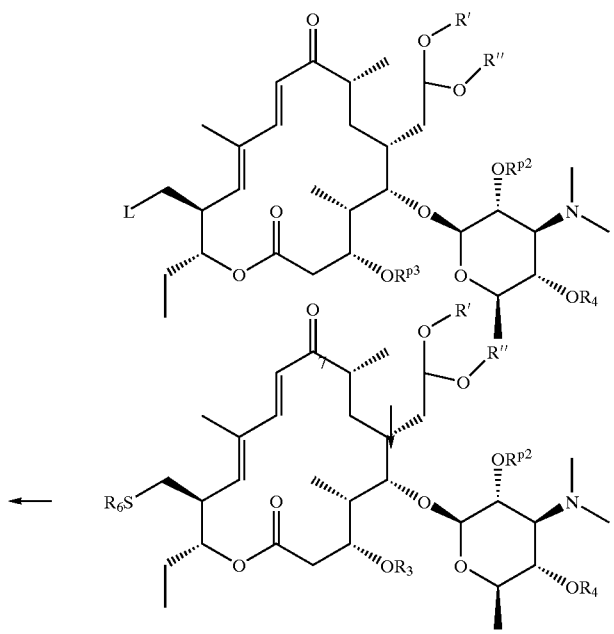

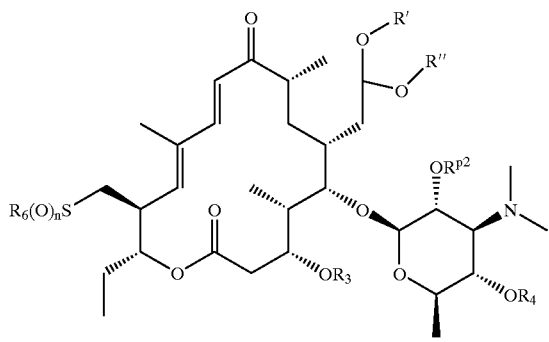

24 n = 1,2

23

Another process of the invention for the preparation of the compounds of Formula I comprises derivatization of 7 of Scheme 7 to 23 by treating with a mercaptan such as methyl mercaptan, benzenethiol, benzyl mercaptan, or the like, in an organic solvent such as acetonitrile, THF, methylene chloride, or the like or mixtures thereof, at from about −20° C. to about 100° C., optionally containing water (1–90% in volume), in the presence of a base such as lutidine, DBU, DMAP, sodium hydroxide, potassium hydroxide, sodium hydride, potassium hydride, potassium tert-butoxide, potassium hydroxide, KHMDS, or the like, optionally added a phase-transfer catalyst such as tetrabutylammonium iodide, benzyltriethylammonium chloride, n-cetyltrimethylammonium bromide, tetraphenylphosphonium bromide, 18-crown-6, or the like. 23 can be further oxidized to 24 where n=1 or 2 with an oxidant such as PCC, PDC, chromium trioxide, $MnO_2$, $RuO_4$, oxone, or the like, at about −45° C. to about 25° C. for about 1 to 48 hours. 23 and 24 can be deprotected as previously described to give compounds of Formula I.

EXAMPLES

The synthetic methods described above for preparation of compounds of Formula I of the present invention will be better understood in connection with the following examples, which are intended to be illustrative only, and not limiting of the scope of the invention. Various changes and modifications to the disclosed embodiments will be apparent to those skilled in the art. Such changes and modifications, including without limitation, those relating to the chemical structures, substituents, derivatives, syntheses, formulations and/or methods of the invention may be made without departing from the spirit of the invention and the scope of the appended claims.

Example 1

Compound of Formula I: A=—CHO, B=—$CH_2N(CH_3)_2$, $R_1$ and $R_2$ taken together are=O, $R_3$=H, $R_4$=H, and $R^P$=H Step 1a. Compound Formula I: A=—$CH(OCH_3)_2$, B=—$CH_2OH$, $R_1$ and $R_2$ taken together are=O, $R_3$=H, $R_4$=—$COCH_3$ and $R^P$=—$COCH_3$ Into a solution of the compound of formula I, where A=CHO, B=—$CH_2OH$, $R_1$ and $R_2$ taken together are=O, $R_3$=H, $R_4$=—$COCH_3$ and $R^P$=—$COCH_3$ (6.1 g, 8.9 mmol) in methanol (20 mL), was added dropwise at 0° C. a solution of acetic chloride (2 mL) in methanol (10 mL). The reaction mixture was stirred for 40 minutes at 0° C. After addition of a solution of saturated sodium bicarbonate, the mixture was extracted with ethyl acetate. The extract was washed with brine, dried ($Na_2SO_4$), filtered and concentrated under reduced pressure to give the title compound (6.3 g, 97%) as a white solid.

MS (ESI) m/z 728 (M+H)$^+$.

$^{13}$C-NMR(100 MHz, $CDCl_3$): δ203.9, 173.6, 169.7, 169.2, 155.3, 147.4, 141.6, 135.7, 118.6, 102.4, 102.0, 81.2, 74.9, 71.5, 70.9, 70.5, 67.1, 62.2, 60.3, 53.5, 49.9, 47.1, 41.1, 39.7, 32.8, 30.9, 25.2, 21.3, 21.1, 20.9, 17.7, 17.1, 14.1, 13.0, 9.6, 8.6.

Step 1b. Compound of Formula I: A=—$CH(OCH_3)_2$, B=—$CH_2OMs$, $R_1$ and $R_2$ taken together are=O, $R_3$=H, $R_4$=—$COCH_3$ and $R^P$=—$COCH_3$ Into the solution of the compound from step 1a (5.00 g, 6.87 mmol) in dichloromethane (20 mL), was added methanesulfonic anhydride (1.32 g, 7.56 mmol) and triethylamine (1.04 g, 10.30 mmol) at 0° C. The reaction mixture was stirred for 5 minutes, then warmed up to room temperature and stirred for 2 hrs. The reaction mixture was again cooled to 0° C. Additional methanesulfonic anhydride (70 mg, 0.40 mmol) was added. The mixture was stirred for 30 minutes, quenched by addition of water (200 mL) and extracted with dichloromethane. The extract was dried ($Na_2SO_4$), filtered and concentrated under reduced pressure to give essentially pure title compound (5.50 g, 6.82 mmol).

MS (ESI) m/z 806 (M+H)$^+$.

$^{13}$C-NMR(100 MHz, $CDCl_3$): δ203.5, 173.4, 169.7, 169.2, 149.1, 146.5, 138.1, 136.3, 119.5, 102.3, 102.0, 82.9, 81.1, 73.7, 71.4, 70.9, 70.5, 67.7, 67.1, 53.5, 53.4, 49.8, 47.0, 44.9, 44.0, 41.1, 39.6, 37.5, 30.8, 25.1, 21.2, 21.1, 17.6, 17.1, 14.1, 13.0, 9.4, 8.6.

Step 1c. 7 of Scheme 1: L=I, $R^P_2$=—$COCH_3$, $R^P_3$=H, $R_4$=—$COCH_3$, and R'=R"=—$CH_3$ Into a solution of the compound from step 1b (5.50 g, 6.82 mmol) in acetone (20 mL), was added NaI (8.3 g, 55 mmol) at room temperature. The mixture was stirred under $N_2$, with the absence of light for 16 hours. The mixture was taken up in $CHCl_3$, washed with water, dried ($Na_2SO_4$), filtered and concentrated under reduced pressure to give the crude title compound (6.0 g). The pure title compound can be obtained by further purification on silica (EtOAc:Hexanes/1:1).

MS (ESI) m/z 838 (M+H)$^+$.

$^{13}$C-NMR(100 MHz, $CDCl_3$): δ203.7, 173.4, 169.7, 169.2, 146.9, 142.4, 135.5, 119.2, 102.4, 102.1, 81.2, 76.8, 71.5, 70.9, 70.5, 67.2, 60.3, 53.5, 49.9, 45.6, 41.2, 39.7, 32.8, 30.9, 24.7, 21.3, 21.2, 20.9, 17.7, 17.1, 14.1, 13.2, 14.1, 13.2, 9.5, 8.6.

Step 1d. 8 of Scheme 1: $R_4$=—$COCH_3$, $R_5$=$R_6$=—$CH_3$, $R^P_2$=—$COCH_3$, $R^P_3$=H, and R'=R"=—$CH_3$ Into the solution of the crude compound from step 1c (6.0 g) in acetonitrile (50 mL), was added excess dimethylamine (17.2 mL of 2 M solution in THF, 34.3 mmol) at room temperature. The reaction mixture was heated to 60° C. for 1.5 hours, cooled to room temperature, stirred overnight, and concentrated under reduced pressure. The resulting crude residue was taken up in $CHCl_3$, washed with saturated $NaHCO_3$ aqueous solution, dried ($Na_2SO_4$), filtered and concentrated under reduced pressure to give the title compound (5.20 g).

MS (ESI) m/z 755 (M+H)$^+$.

$^{13}$C-NMR(100 MHz, $CDCl_3$): δ203.6, 173.6, 169.7, 169.2, 147.7, 144.6, 134.2, 102.4, 102.1, 81.4, 76.2, 71.5, 70.9, 70.6, 67.2, 61.0, 53.5, 49.9, 45.8, 43.3, 41.2, 39.6, 31.5, 31.0, 25.6, 21.3, 21.2, 17.7, 17.2, 14.0, 12.9, 9.6, 8.7.

Step 1e. Compound of Formula I: A=—CHO, B=—$CH_2N(CH_3)_2$, $R_1$ and $R_2$ taken together are=O, $R_3$=H, $R_4$=—$COCH_3$, and $R^P$=—$COCH_3$ Into a solution of the compound from step 1d (80 mg) in THF (1 mL) was added 1N HCl (1 mL). The mixture was stirred for 2 hours at room temperature, then was basified with a solution of saturated sodium bicarbonate and extracted with chloroform. The extract was dried ($Na_2SO_4$), filtered and concentrated under reduced pressure to give pure title compound (65 mg).

MS (ESI) m/z 709 (M+H)$^+$.

$^{13}$C-NMR(100 MHz, ($CDCl_3$): δ203.0, 173.7, 169.7, 169.2, 148.2, 144.5, 134.4, 117.7, 101.8, 80.8, 76.3, 71.4, 71.0, 70.5, 67.9, 67.1, 66.6, 61.1, 53.4, 45.8, 45.0, 43.5, 43.3, 41.2, 40.7, 39.3, 31.6, 31.0, 25.7, 25.5, 2 1.3, 21.2, 17.4, 17.2, 13.0, 9.6, 8.5.

Step 1f. Compound of Formula I A=CHO, B=—$N(CH_3)_2$, $R_1$ and $R_2$ taken together are=O, $R_3$H, $R_4$=H, and $R^P$=H A solution of the compound from Step 1e (65 mg) in methanol (1 mL) was stirred at room temperature for twelve hours, and the solvent evaporated under reduced pressure to give the title compound (63 mg).

MS (ESI) m/z 625 (M+H)$^+$.

$^{13}$C-NMR(100 MHz, CDCl$_3$): δ203.1 (2×), 173.8, 148.3, 144.6, 134.4, 117.9, 103.9, 77.2, 76.3, 73.3, 70.9, 70.8, 70.0, 61.1, 53.4, 50.6, 45.8, 44.8, 43.7, 43.3, 41.6, 39.3, 30.2, 29.6, 25.8, 17.7, 17.4, 12.9, 9.6, 8.9

Example 2

Compound of Formula I: A=—CHO, B=—CH$_2$NH—CH$_2$CH$_2$Phenyl, R$_1$ and R$_2$ taken together are=O, R$_3$=H, R$_4$=H, and R$^P$=H Step 2a. 8 of Scheme 1: R$_4$=—COCH$_3$, R$_5$=—CH$_2$CH$_2$Phenyl, R$_6$=H, R$^P{}_2$=—COCH$_3$, R$^P{}_3$=H, and R'=R"=—CH$_3$ Into a solution of the compound from step 1c (150 mg, 0.18 mmol) in DMF (0.5 mL), was added phenethylamine (24 mg, 0.2 mmol) at room temperature. The reaction mixture was heated at 80° C. for 7 hours, cooled to room temperature and stirred overnight. The mixture was taken up in EtOAc, washed with a saturated aqueous solution of NaHCO$_3$, washed with brine and dried (Na$_2$SO$_4$), filtered and concentrated under reduced pressure to provide the crude product (155 mg). The crude residue was further purified by flash chromatography (EtOAc:Hexanes/1:1) to give the title compound (59 mg).

MS (ESI) m/z 831 (M+H)$^+$.

$^{13}$C-NMR(100 MHz, CDCl$_3$): δ203.8, 173.7, 169.7, 169.2, 147.1, 142.7, 139.6, 136.4, 128.5, 128.4, 126.3, 118.7, 102.4, 102.1, 81.3, 75.8, 71.5, 70.9, 70.6, 67.2, 53.5, 51.3, 50.3, 49.9, 45.5, 45.0, 41.2, 39.7, 36.2, 31.5, 30.9, 29.6, 25.3, 22.6, 21.3, 21.2, 17.7, 17.2, 14.0, 13.0, 9.6, 8.7

Step 2b. Compound of Formula I: A=—CHO, B=—CH$_2$NH—CH$_2$CH$_2$Phenyl, R$_1$ and R$_2$ taken together are=O, R$_3$=H, R$_4$=—COCH$_3$ and R$^P$=—COCH$_3$ Into a solution of the compound of step 2a (59 mg) in THF (1 mL), was added 1N HCl (1 mL) dropwise. The reaction mixture was stirred for 40 minutes at room temperature, then was basified with a solution of saturated sodium bicarbonate and extracted with ethyl acetate. The extract was washed with brine, dried (Na$_2$SO$_4$), filtered and concentrated under reduced pressure. The crude residue was purified by flash chromatography (NH$_4$OH:MeOH:CH$_2$Cl$_2$/1:5:194) to give the title compound (46 mg).

MS (ESI) m/z 785 (M+H)$^+$.

Step 2c. Compound of Formula I: A=—CHO, B=—CH$_2$NH—CH$_2$CH$_2$Phenyl, R$_1$ and R$_2$ taken together are=O, R$_3$H, R$_4$=H, and R$^P$=H A solution of the compound of step 2b (46 mg) in methanol was stirred at room temperature for twelve hours. The solvent was evaporated under reduced pressure to give the title compound.

MS (ESI) m/z 701 (M+H)$^+$.

Example 3

Compound of Formula I: A=—CHO, B=—CH$_2$—N(CH$_3$)—CH$_2$CH$_2$Phenyl, R$_1$ and R$_2$ taken together are=O, R$_3$=H, R$_4$=H, and R$^P$=H Step 3a. 8 of Scheme 1: R$_4$=—COCH$_3$, R$_5$=—CH$_2$CH$_2$Phenyl, R$_6$=—CH$_3$, R$^P{}_2$=—COCH$_3$, R$^P{}_3$=H, and R'=R"=—CH$_3$ Into a solution of the crude compound from step 2a (155 mg) in acetonitrile (1.5 mL), was added formaldehyde (0.1 mL, 40% in water), acetic acid (0.1 mL) and NaCNBH$_3$ (56 mg, 0.9 mmol) at 0° C. The solution was stirred at 0° C. for 20 minutes, then warmed to room temperature and stirred for three hours. The reaction mixture was basified with a solution of saturated sodium bicarbonate and extracted with ethyl acetate. The extract was washed with brine, dried (Na$_2$SO$_4$), filtered and concentrated under reduced pressure. The crude compound was purified by flash chromatography (NH$_4$OH:MeOH:CH$_2$Cl$_2$/1:5:94) to give the title compound (33 mg) as a white foam.

MS (ESI) m/z 845 (M+H)$^+$.

Step 3b. Compound of Formula I: A=—CHO, B=—CH$_2$N(CH$_3$)—CH$_2$CH$_2$Phenyl, R$_1$ and R$_2$ taken together are=O, R$_3$=H, R$_4$=—COCH$_3$ and R$^P$=—COCH$_3$ Into a solution of the compound of step 3a (33 mg) in THF (1 mL), was added 1N HCl (1 mL) dropwise. The reaction mixture was stirred for 40 minutes at room temperature, then was basified with a solution of saturated sodium bicarbonate and extracted with ethyl acetate. The extract was washed with brine, dried (Na$_2$SO$_4$), filtered and concentrated under reduced pressure to give pure title compound (30 mg).

MS (ESI) m/z 799 (M+H)$^+$.

$^{13}$C-NMR(100 MHz, CDCl$_3$): δ203.2, 203.1, 173.8, 169.8, 169.2, 148.2, 144.8, 140.2, 134.1, 128.6, 128.3, 126.0, 117.7, 101.8, 80.8, 76.5, 71.4, 71.0, 70.5, 67.1, 66.7, 59.7, 58.9, 55.4, 45.0, 43.5, 43.3, 41.2, 40.7, 39.3, 33.6, 31.6, 31.1, 25.8, 21.3, 21.2, 17.5, 17.2, 13.0, 9.7, 8.6

Step 3c. Compound of Formula I: A=—CHO, B=—CH$_2$N(CH$_3$)—CH$_2$CH$_2$Phenyl, R$_1$ and R$_2$ taken together are=O, R$_3$=H, R$_4$=H and R$^P$=H A solution of the compound from step 3b (30 mg) in methanol (1 mL) was stirred at room temperature overnight, then concentrated under reduced pressure to give the pure title compound (27 mg).

MS (ESI) m/z 715 (M+H)$^+$.

$^{13}$C-NMR(100 MHz, CDCl$_3$): δ203.1, 202.9, 173.9, 148.3, 144.9, 140.2, 134.1, 128.7, 128.6, 128.3, 126.0, 104.0, 73.3, 70.9, 70.7, 70.2, 59.7, 59.1, 44.7, 43.8, 43.3, 42.5, 41.7, 41.2, 40.6, 39.3, 35.5, 33.6, 29.7, 25.9, 23.3, 17.8, 17.4, 12.9, 9.7, 8.9.

Example 4

Compound of Formula I: A=—CHO, B=—CH$_2$—NH—CH$_2$CH$_2$-(2-pyridyl), R$_1$ and R$_2$ taken together are=O, R$_3$=H, R$_4$=H and R$^P$=H Step 4a. 8 of Scheme 1: R$_4$=—COCH$_3$, R$_5$=—CH$_2$CH$_2$-(2-pyridyl), R$_6$=H, R$^P{}_2$=—COCH$_3$, R$^P{}_3$=H, and R'=R"=—CH$_3$ The compound from step 1c (300 mg, 0.36 mmol) was treated with 2-(2-aminoethyl)pyridine (48 mg, 0.39 mmol) by following procedure described in step 2a to give the pure title compound (100 mg).

MS (ESI) m/z 832 (M+H)$^+$.

$^{13}$C-NMR(100 MHz, CDCl$_3$): δ203.7, 173.7, 169.7, 169.2, 159.7, 149.2, 147.0, 142.4, 136.5, 136.4, 123.2, 121.4, 102.4, 102.0, 81.2, 77.2, 75.7, 71.5, 70.9, 70.5, 67.2, 53.4, 50.0, 49.9, 49.1, 45.1, 44.9, 41.2, 41.1, 39.7, 37.3, 32.8, 32.6, 30.9, 25.2, 21.3, 21.1, 17.6, 17.1, 13.1, 9.6, 8.6.

Step 4b. 8 of Scheme 1: R$_4$=—COCH$_3$, R$_5$=—CH$_2$CH$_2$-(2-pyridyl), R$_6$=—CH$_3$, R$^P{}_2$=—COCH$_3$, R$^P{}_3$=H, and R'=R"=—CH$_3$ Into a solution of the compound from step 4a (57 mg, 0.068 mmol) in acetonitrile (1.5 mL), was added formaldehyde (0.1 mL, 40% in water), acetic acid (0.1 mL) and NaCNBH$_3$ (56 mg, 0.9 mmol) at 0° C. The solution was stirred at 0° C. for 20 minutes, then warmed to room temperature and stirred for three hours. The reaction mixture was basified with a solution of saturated sodium bicarbonate and extracted with ethyl acetate. The extract was washed with brine, dried (Na$_2$SO$_4$), filtered and concentrated under reduced pressure. The crude compound was purified by flash chromatography (NH$_4$OH: MeOH:CH$_2$Cl$_2$/1:5:94) to give the title compound (33 mg) as a white foam.

MS (ESI) m/z 846 (M+H)$^+$.

$^{13}$C-NMR(100 MHz, CDCl$_3$): δ203.8, 173.7, 169.7, 169.3, 160.3, 149.1, 147.8, 136.3, 133.9, 123.3, 121.2, 102.5, 102.1, 81.4, 76.5, 71.6, 71.0, 70.6, 67.3, 60.3, 58.8, 57.8, 53.5, 50.0, 45.0, 43.3, 42.3, 41.2, 39.7, 35.8, 32.7, 31.0, 29.7, 25.6, 21.3, 21.2, 17.7, 17.2, 14.2, 12.9, 9.7, 8.7.

Step 4c. Compound of Formula I: A=—CHO, B=—CH$_2$N(CH$_3$)—CH$_2$CH$_2$-(2-pyridyl), R$_1$ and R$_2$ taken together are=O, R$_3$=H, R$_4$=—COCH$_3$ and R$_p$=—COCH$_3$ Into a solution of the compound of step 4b (33 mg) in THF (1 mL), was added 1N HCl (1 mL) dropwise. The reaction mixture was stirred for 40 minutes at room temperature, then was basified with a solution of saturated sodium bicarbonate and extracted with ethyl acetate. The extract was washed with brine, dried (Na$_2$SO$_4$), filtered and concentrated under reduced pressure to give pure title compound (30 mg).

MS (ESI) m/z 800 (M+H)$^+$.

$^{13}$C-NMR(100 MHz, CDCl$_3$): δ203.2, 203.1, 173.8, 169.7, 169.2, 160.2, 149.2, 148.2, 136.3, 134.0, 123.3, 121.2, 101.8, 80.8, 76.5, 71.4, 71.0, 70.5, 67.1, 66.6, 58.9, 57.8, 45.0, 43.5, 43.2, 42.2, 41.2, 40.7, 39.3, 35.7, 31.6, 31.1, 25.7, 21.3, 21.2, 17.5, 17.2, 12.9, 9.7, 8.5.

Step 4d. Compound of Formula I: A=—CHO, B=—CH$_2$N(CH$_3$)—CH$_2$CH$_2$-(2-pyridyl), R$_1$ and R$_2$ taken together are= O, R$_3$=H R$_4$=H and R$^P$=H A solution of the compound from step 4c (30 mg) in methanol (1 mL) was stirred at room temperature overnight, then concentrated under reduced pressure to give the pure title compound (28 mg).

MS (ESI) m/z 716 (M+H)$^+$.

$^{13}$C-NMR(100 MHz, CDCl$_3$): δ203.7, 203.1, 173.9, 160.2, 149.2, 148.3, 136.3, 134.0, 123.3, 121.2, 104.0, 73.3, 71.0, 70.8, 70.2, 59.1, 57.9, 53.4, 44.7, 43.8, 43.3, 42.3, 41.7, 39.3, 35.8, 29.7, 25.9, 17.8, 17.4, 12.9, 9.7, 9.0.

Example 5

Compound of Formula I: A=—CHO, B=—CH-4-morpholyl, R$_1$ and R$_2$ taken together are=O, R$_3$=H, R$_4$=H and R$^P$=H Step 5a. 8 of Scheme 1: R$_4$=—COCH$_3$, R$_5$ and R$_6$ taken together=—CH$_2$CH$_2$—O—CH$_2$CH$_2$—, R$^P_2$=—COCH$_3$, R$^P_3$=H, and R'=R"=—CH$_3$ Into the solution of the crude compound from step 1c (200 mg, 0.238 mmol) in acetonitrile (2 mL), was added morpholine (104 mg, 1.2 mmol) at room temperature. The reaction mixture was heated to 60° C. for 4.5 hours, cooled to room temperature, stirred overnight. The reaction mixture was taken up in EtOAc, washed with brine, dried (Na$_2$SO$_4$), filtered and concentrated under reduced pressure. The crude compound was purified by flash chromatography (MeOH:CH$_2$Cl$_2$/2:98) to give the title compound (157 mg) as a white foam.

MS (ESI) m/z 797 (M+H)$^+$.

$^{13}$C-NMR(100 MHz, CDCl$_3$): δ203.8, 173.6, 169.6, 169.1, 147.5, 144.3, 133.7, 118.2, 102.3, 102.0, 81.2, 76.3, 71.4, 70.9, 70.5, 67.1, 66.6, 59.9, 53.8, 53.4, 53.3, 49.8, 44.9, 42.3, 41.1, 39.6, 32.8, 32.6, 30.9, 25.5, 21.2, 21.1, 17.6, 17.1, 12.8, 9.6, 8.6.

Step 5b Compound of Formula I: A=—CHO, B=—CH$_2$-4-morpholyl, R$_1$ and R$_2$ taken together are=O, R$_3$=H, R$_4$=—COCH$_3$ and R$^P$=—COCH$_3$ Into a solution of the compound of step 5a (157 mg) in THF (1 mL), was added 1N HCl (1 mL) dropwise. The reaction mixture was stirred for 40 minutes at room temperature, then was basified with a solution of saturated sodium bicarbonate and extracted with ethyl acetate. The extract was washed with brine, dried (Na$_2$SO$_4$), filtered and concentrated under reduced pressure to give pure title compound (150 mg).

MS (ESI) m/z 751 (M+H)$^+$.

$^{13}$C-NMR(100 MHz, CDCl$_3$): δ203.2, 202.9, 173.6, 169.6, 169.1, 147.9, 144.4, 133.8, 117.8, 101.6, 80.6, 76.3, 71.3, 70.9, 70.3, 66.9, 66.6, 66.5, 60.2, 60.0, 53.8, 44.9, 43.4, 42.2, 41.1, 40.6, 39.2, 31.5, 30.9, 25.6, 21.1, 21.0, 20.8, 17.4, 17.1, 14.0, 12.8, 9.6, 8.4.

Step 5c. Compound of Formula I: A=—CHO, B=—CH$_2$-4-morpholyl, R$_1$ and R$_2$ taken together are=O, R$_3$=H, R$_4$=H, and R$^P$=H A solution of the compound from step 5b (150 mg) in methanol (4 mL) was stirred at room temperature overnight, then concentrated under reduced pressure to give the pure title compound (125 mg).

MS (ESI) m/z 667 (M+H)$^+$.

$^{13}$C-NMR(100 MHz, CDCl$_3$): δ203.3, 203.0, 173.8, 148.1, 144.6, 133.8, 103.9, 76.4, 73.2, 70.8, 70.7, 70.0, 66.7, 60.1, 53.8, 50.5, 44.7, 43.6, 42.3, 41.6, 39.3, 25.7, 17.7, 17.4, 12.8, 9.6, 8.9.

Example 6

Compound of Formula I: A=—CHO, B=—CH$_2$-1-imidazolyl, R$_1$ and R$_2$ taken together are =O, R$_3$=H, and R$^P$=H Step 6a. 8 of Scheme 1: R$_4$=—COCH$_3$, R$_5$ and R$_6$ taken together=—CHNCH=CH—, R$^P_2$=—COCH$_3$, R$^P_3$=H, and R'=R"=—CH$_3$ Into the solution of the crude compound from step 1c (150 mg, 0.179 mmol) in acetonitrile (1 mL), was added imidazole (85 mg, 1.25 mmol) at room temperature. The reaction mixture was heated to 60° C. for 4 hours, cooled to room temperature, stirred overnight. The reaction mixture was taken up in CHCl$_3$, washed with water and brine, dried (Na$_2$SO$_4$), filtered and concentrated under reduced pressure. The crude compound was purified by flash chromatography (MeOH:CH$_2$Cl$_2$, 2:98) to give the title compound (37 mg) as a white foam.

MS (ESI) m/z 778 (M+H)$^+$.

Step 6b. 8 of Scheme 1: R$_4$=H, R$_5$ and R$_6$ taken together=—CHNCH=CH—, R$^P_2$=H, R$^P_3$=H, and R'=R"=—CH$_3$ A solution of the compound from step 6a (37 mg) in methanol is stirred at room temperature for twelve hours and the solvent evaporated under reduced pressure to give the title compound (35 mg).

MS (ESI) m/z 694 (M+H)$^+$.

Step 6c. Compound of Formula I: A=—CHO, B=—CH$_2$-1-imidazolyl, R$_1$ and R$_2$ taken together are=O, R$_3$=H, R$_4$=H, and R$^P$=H Into a solution of the compound of step 6b (35 mg) in THF (1 mL), was added 1N HCl (1 mL) dropwise. The reaction mixture was stirred for 40 minutes at room temperature, then was basified with a solution of saturated sodium bicarbonate and extracted with ethyl acetate. The extract was washed with brine, dried (Na$_2$SO$_4$), filtered and concentrated under reduced pressure to give pure title compound (32 mg).

MS (ESI) m/z 648 (M+H)$^+$.

$^{13}$C-NMR(100 MHz, CDCl$_3$): δ203.0, 202.8, 173.6, 146.8, 139.4, 137.1, 136.9, 129.8, 118.8, 103.9, 74.6, 73.3, 70.9, 70.7, 70.1, 60.3, 47.8, 46.8, 44.5, 43.7, 41.7, 39.4, 25.5, 17.8, 17.2, 12.7, 9.6, 8.9.

Example 7

Compound of Formula I: A=—CHO, B=—CH$_2$-N(CH$_3$)$_2$, R$_1$ and R$_2$ taken together are=O, R$_3$=H, R$_4$=—CH$_2$CHCH-(3-quinolyl), and R$^P$=H Step 7a. 8 of Scheme 1: R$_4$=—COCH$_3$, R$_5$=R$_6$=—CH$_3$, R$^P_2$=—COCH$_3$, R$^P_3$=TMS, and R'=R"=—CH$_3$ To the crude compound from step 1d (5.2 g, 6.82 mmol) in 1-methylimidazole (20 mL), was added 1,1,1,3,3,3-hexamethyl disilazane (1.72 mL, 8.16 mmol). After stirring at room temperature for 5.5 hrs, the reaction mixture was diluted with ethyl acetate, washed with water, then with brine, and dried (Na$_2$SO$_4$), filtered and concentrated under reduced pressure to give a yellow syrup. The compound was purified by flash chromatography (ethyl acetate) to give 4.6 g of the title compound (82% from the compound of step 1b).

MS (ESI) m/z 827 (M+H)$^+$.

$^{13}$C-NMR(100 MHz, CDCl$_3$): δ203.7, 171.5, 169.5, 169.0, 147.5, 144.4, 133.6, 118.3, 101.7, 100.4, 78.4, 76.0, 71.4, 70.7, 70.3, 68.1, 67.1, 60.8, 53.6, 49.0, 45.6, 43.3, 41.6, 41.1, 36.2, 32.7, 32.1, 29.5, 25.5, 21.2, 21.0, 17.7, 17.2, 13.9, 12.7, 9.5, 8.7, 0.2.

Step 7b. 8 of Scheme 1: R$_4$=H, R$_5$=R$_6$=—CH$_3$, R$^P_2$=H, R$^P_3$=TMS, and R'=R''=—CH$_3$ A mixture of the compound from step 7a (4.5 g, 5.4 mmol) and methanol (40 mL) was stirred at room temperature overnight and concentrated under reduced pressure to give 4.0 g of the title compound.

MS (ESI) m/z 743 (M+H)$^+$.

$^{13}$C-NMR(100 MHz, CDCl$_3$): δ203.8, 171.6, 147.9, 144.7, 133.7, 118.5, 102.7, 101.8, 78.4, 76.1, 73.1, 71.3, 70.6, 70.1, 68.4, 61.0, 53.7, 45.8, 43.4, 41.7, 36.7, 33.4, 32.3, 25.6, 21.3, 21.2, 17.9 (2C), 12.8, 9.6, 9.4, 0.3.

Step 7c. Compound of Formula I: A=—CH(OCH$_3$)$_2$, B=—CH$_2$N(CH$_3$)$_2$, R$_1$ and R$_2$ taken together are=O, R$_3$=TMS, R$_4$=—CH$_2$CHCH-(3-quinolyl), and R$^P$H Into a degassed solution of the compound from step 7b (410 mg, 0.55 mmol) and 1-(3-quinolyl)-2-propen-1-ol-t-butyl carbonate (171 mg, 0.60 mmol) in THF (4 mL) were added Pd$_2$(dba)$_3$ (46 mg, 0.05 mmol), and dppb (42 mg, 0.1 mmol). The mixture was stirred at room temperature for 15 mins, heated to 65° C. for 2 hrs, then cooled to room temperature. The mixture was filtered through a short plug of silica gel (eluting with ethylacetate). The eluant was concentrated under reduced pressure to provide the resulting crude mixture of the title compound (120 mg).

MS (ESI) m/z 910 (M+H)$^+$.

Step 7d. Compound of Formula I: A=—CHO, B=—CH$_2$N(CH$_3$)$_2$, R$_1$ and R$_2$ taken together are=O, R$_3$=H, R$_4$=—CH$_2$CHCH-(3-quinolyl), and R$^P$=H Into a solution of the crude compound from step 7c (120 mg) in THF (1 mL) at 0° C. was added 1N HCl (1 mL). The mixture was stirred at 0° C. for 2 hrs and quenched by addition of a saturated solution of NaHCO$_3$. The resulting aqueous solution was extracted with CHCl$_3$. The extract was concentrated under reduced pressure. The crude residue was purified on reversed phase HPLC to give the title compound.

MS (ESI) m/z 792 (M+H)$^+$.

$^{13}$C-NMR(100 MHz, CDCl$_3$): δ203.5, 174.2, 149.4, 148.4, 147.6, 144.8, 134.7, 132.9, 129.5 (2C), 129.4, 128.9, 128.4, 128.0, 127.2, 117.9, 103.8, 102.4, 81.7, 80.0, 76.5, 73.3, 71.9, 70.4, 70.1, 67.2, 61.3, 46.0, 45.3, 44.0, 43.6, 41.9, 41.1, 39.7, 32.7, 31.5, 26.0, 18.3, 17.7, 13.1, 9.9, 9.0.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the Formula:

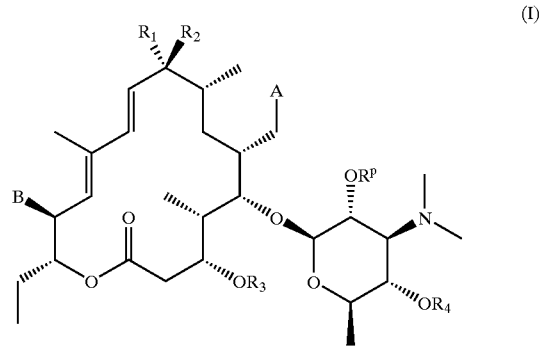

(I)

wherein

A is selected from the group consisting of:

(1) —CHO or a protected aldehyde;

(2) —CN;

(3) —CH═N—NR$_5$R$_6$, wherein R$_5$ and R$_6$ are each independently selected from the group consisting of:
   a. hydrogen,
   b. C$_1$–C$_6$-alkyl, optionally substituted with one or more substituents selected from the group consisting of halogen, aryl, substituted aryl, heterocyclic and substituted heterocyclic,
   c. C$_2$–C$_6$-alkenyl, optionally substituted with one or more substituents selected from the group consisting of: halogen, aryl, substituted aryl, heterocyclic and substituted heterocyclic,
   d. C$_2$–C$_6$-alkynyl, optionally substituted with one or more substituents selected from the group consisting of: halogen, aryl, substituted aryl, heterocylic and substituted heterocyclic, and
   e. R$_5$ and R$_6$ taken together with the nitrogen atom to which they are connected form a 3- to 7-membered ring which may optionally contain one or more heterofunctions selected from the group consisting of: —O—, —NH—, —N(C$_1$-C$_6$-alkyl)—, —N(aryl)—, —N(heteroaryl)—, —S—, —S(O)— and —S(O)$_2$—;

(4) —CH═N—OR$_5$, wherein R$_5$ is as previously defined;

(5) —CH$_3$X, wherein X is selected from the group consisting of:
   (a) hydroxy or protected hydroxy;
   (b) halogen;
   (c) —NR$_5$R$_6$, wherein R$_5$ and R$_6$ are as previously defined;
   (d) —NR$_5$C(O)—R$_7$, where R$_5$ is as previously defined and R$_7$ is selected from the group consisting of:
      i. hydrogen;
      ii. C$_1$–C$_6$-alkyl, optionally substituted with one or more substituents selected from the group consisting of: halogen, aryl, substituted aryl, heterocyclic and substituted heterocyclic;
      iii. C$_2$–C$_6$-alkenyl, optionally substituted with one or more substituents selected from the group consisting of: halogen, aryl, substituted aryl, heterocylic and substituted heterocyclic;
      iv. C$_2$–C$_6$-alkynyl, optionally substituted with one or more substitueuts selected from the group consisting of: halogen, aryl, substituted aryl, heterocyclic and substituted heterocyclic;

v. aryl;
vi. substituted aryl;
vii. heterocyclic; and
viii. substituted heterocyclic;
(e) —$NR_5C(O)$—$NR_6R_7$, where $R_5$, $R_6$, and $R_7$ are as previously defined;
(f) —$NR_5$—$NR_6R_7$, where $R_5$, $R_6$ and $R_7$ are as previously defined;
(g) —$NR_5$—$NR_6C(O)$—$R_7$, where $R_5$, $R_6$ and $R_7$ are as previously defined;
(h) —$S(O)_n$—$R_8$, where $R_8$ is selected from the group consisting of: aryl, substituted aryl, heterocyclic and substituted heterocyclic, where n=0, 1 or 2;
(i) —$S(O)_n$—($C_1$–$C_6$-alkyl), optionally substituted with one or more substituents selected from the group consisting of: halogen, aryl, substituted aryl, heterocyclic and substituted heterocyclic, where n is as previously defined;
(j) —$S(O)_n$—($C_2$–$C_6$-alkenyl), optionally substituted with one or more substituents selected from the group consisting of: halogen, aryl, substituted aryl, heterocyclic and substituted heterocyclic, where n is as previously defined;
(k) —$S(O)_n$—($C_2$–$C_6$-alkynyl), optionally substituted with one or more substituents selected from the group consisting of: halogen, aryl, substituted aryl, heterocyclic and substituted heterocyclic, where n is as previously defined; and
(l) —O—M—Y, where M is:
i. absent,
ii. —C(O)—,
iii. —C(O)N($R_5$)—, where $R_5$ is as previously defined,
iv. $C_1$–$C_6$-alkyl-N($R_5$)—, where $R_5$ is as previously defined,
v. $C_2$–$C_6$-alkenyl-N($R_5$)—, where $R_5$ is as previously defined, or
vi. $C_2$–$C_6$-alkynyl-N($R_5$)—, where $R_5$ is as previously defined,
and Y is:
i. hydrogen,
ii. $C_1$–$C_6$-alkyl, optionally substituted with one or more substituents selected from the group consisting of halogen, —$OR_5$, aryl, substituted aryl, heterocyclic and substituted heterocyclic, where $R_5$ is as previously defined,
iii. $C_2$–$C_6$-alkenyl, optionally substituted with one or more substituents selected from the group consisting of halogen, —$OR_5$, aryl, substituted aryl, heterocyclic and substituted heterocyclic, where $R_5$ is as previously defined.
iv. $C_2$–$C_6$-alkynyl, optionally substituted with one or more substituents selected from the group consisting of halogen, —$OR_5$, aryl, substituted aryl, heterocyclic and substituted heterocyclic, where $R_5$ is as previously defined,
v. aryl,
vi. substituted aryl,
vii. heterocyclic, or
viii. substituted heterocyclic; and
(6) heterocyclic or substituted heterocyclic;
B is selected from the group consisting of:
(1) —CHO or a protected aldehyde;
(2) —CN;
(3) —CH=N—$NR_5R_6$, wherein $R_5$ and $R_6$ are as previously defined;
(4) —CH=N—$OR_5$, wherein $R_5$ is as previously defined;
(5) —$CH_2Z$, wherein Z is selected from the group consisting of:
a. halogen;
b. —$NR_5C(O)$—$R_7$, where $R_5$ and $R_7$ are as previously defined;
c. —$NR_5C(O)$—$NR_6R_7$, where $R_5$, $R_6$, and $R_7$ are as previously defined;
d. —$NR_5$—$NR_6R_7$, where $R_5$, $R_6$ and $R_7$ are as previously defined;
e. —$NR_5$—$NR_6C(O)$—$R_7$, where $R_5$, $R_6$ and $R_7$ are as previously defined;
f. —$S(O)_n$—$R_8$, where $R_8$ and $n$ are as previously defined;
g. —$S(O)_n$—($C_1$–$C_6$-alkyl), optionally substituted with one or more substituents selected from the group consisting of: halogen, aryl, substituted aryl, heterocyclic and substituted heterocyclic, where n is as previously defined;
h. —$S(O)_n$—($C_2$–$C_6$-alkenyl), optionally substituted with one or more substituents selected from the group consisting of; halogen, aryl, substituted aryl, heterocyclic and substituted heterocyclic, where n is as previously defined;
i. —$S(O)_n$—($C_2$–$C_6$-alkynyl), optionally substituted with one or more substituents selected from the group consisting of: halogen, aryl, substituted aryl, heterocyclic and substituted heterocyclic, where n is as previously defined; and
j. —$NR_9R_{10}$, where $R_9$ and $R_{10}$ are each independently selected from the group consisting of:
(i) hydrogen;
(ii) $C_1$–$C_6$-alkyl, optionally substituted with one or more substituents selected from the group consisting of: halogen, aryl, substituted aryl, heterocyclic, —O—$R_5$ and —$NR_5R6$, where $R_5$ and $R_6$ are as previously defined;
(iii) $C_2$–$C_6$-alkenyl, optionally substituted with one or more substituents selected from the group consisting of: halogen, aryl, substituted aryl, heterocyclic, substituted heterocyclic, —O—$R_5$ and —$NR_5R_6$, where $R_5$ and $R_6$ are as previously defined;
(iv) $C_2$–$C_6$-alkynyl, optionally substituted with one or more substituents selected from the group consisting of: halogen, aryl, substituted aryl, heterocyclic, substituted heterocyclic, O—$R_5$ and $NR_5R_6$, where $R_5$ and $R_6$ are as previously defined; and
(v) —W—$R_{11}$, where W is selected from the group consisting of:
1. —C(O)—;
2. —C(O)O—;
3. —C(S)—;
4. —C(S)—S—;
5. —C(S)—O—;
6. —C(S)—$NR_5$, where $R_5$ is as previously defined;
7. —C(O)$NR_5$, where $R_5$ is as previously defined;
8. —C(=$NR_5$)—O—, where $R_5$ is as previously defined; and
9. —C(=$NR_{11}$)—$NR_5R_6$, where $R_5$ and $R_6$ are as previously defined, and
where $R_{11}$ is selected from the group consisting of:
(a) hydrogen;
(b) $C_1$–$C_6$-alkyl, optionally substituted with one or more substituents selected from the group consisting of: halogen, aryl, substituted aryl, heterocyclic and substituted heterocyclic;
(c) $C_2$–$C_6$-alkenyl, optionally substituted with one or more substituents selected from the group consisting of: halogen, aryl, substituted aryl, heterocyclic and substituted heterocyclic;
(d) $C_2$–$C_6$-alkynyl, optionally substituted with one or more substituents selected from the group consisting of: halogen, aryl, substituted aryl, heterocyclic and substituted heterocyclic;
 (vi) $R_9$ and $R_{10}$ taken together with the nitrogen atom they are attached to represent the carbon or hetero atoms necessary to form a heterocyclic or substituted heterocyclic moiety; and
 (vii) $R_9$ and $R_{10}$ taken together with the nitrogen atom they are attached to form a 4 to 8 membered ring which contains one or more W moieties, and optionally may contain one or more heteromoieties selected from the group consisting of —O—, —S—, —S(O)$_2$— and —NR$_5$—, where W and $R_5$ are as previously defined;
provided that when $R_3$ and $R_4$ are hydrogen, Z cannot be —NR$_9$R$_{10}$;
$R_1$ and $R_2$ are each independently selected from the group consisting of:
(1) hydrogen;
(2) hydroxy;
(3) protected hydroxy;
(4) —OC(O)—$C_1$–$C_{13}$-alkyl, optionally substituted with one or more substituents selected from the group consisting of halogen, aryl, substituted aryl, heterocyclic, substituted heterocyclic, O—R5 and NR$_5$R$_6$ where $R_5$ and $R_6$ are as previously defined;
(5) —O—R5, where $R_5$ is as previously defined;
(6) halogen;
(7) —NR$_5$R$_6$, where $R_5$ and $R_6$ are as previously defined; and
(8) $R_1$ and $R_2$ taken together are oxo;
$R_3$ is selected from the group consisting of:
(1) hydrogen;
(2) a hydroxy protecting group;
(3) —C(O)—$C_1$–$C_{12}$-alkyl, optionally substituted with one or more substituents selected from the group consisting of: halogen, aryl, substituted aryl, heterocyclic, substituted heterocyclic, —OR$_5$ and —NR$_5$R$_6$, where $R_5$ and $R_6$ are as previously defined;
(4) $C_1$–$C_6$-alkyl, optionally substituted with one or more substituents selected from the group consisting of: halogen, aryl, substituted aryl, heterocyclic, substituted heterocyclic, —OR$_5$ and —NR$_5$R$_6$, where $R_5$ and $R_6$ are as previously defined;
(5) $C_2$–$C_6$-alkenyl, optionally substituted with one or more substituents selected from the group consisting of: halogen, aryl, substituted aryl, heterocyclic, substituted heterocyclic, —OR$_5$ and —NR$_5$R$_6$, where $R_5$ and $R_6$ are as previously defined; and
(6) $C_2$–$C_6$-alkynyl, optionally substituted with one or more substituents selected from the group consisting of: halogen, aryl, substituted aryl, heterocyclic, substituted heterocyclic, —OR$_5$ and —NR$_5$R$_6$, where $R_5$ and $R_6$ are as previously defined;
$R_4$ is —M—Y, where M and Y are as previously defined; provided that when M is absent Y can not be mycarosyl or substituted mycarosyl; and
$R^P$ is hydrogen or a hydroxy protecting group.

2. A compound according to claim 1 where $R_3$ is selected from the group consisting of:
(1) $C_1$–$C_6$-alkyl, optionally substituted with one or more substituents selected from the group consisting of: halogen, aryl, substituted aryl, heterocyclic, substituted heterocyclic, —O—R$_5$ and —NR$_5$R$_6$, where $R_5$ and $R_6$ are as defined in claim 1;
(2) $C_2$–$C_6$-alkenyl, optionally substituted with one or more substituents selected from the group consisting of: halogen, aryl, substituted aryl, heterocyclic, substituted heterocyclic, —O—R$_5$ and —NR$_5$R$_6$, where $R_5$ and $R_6$ are as previously defined; and
(3) $C_2$–$C_6$-alkynyl, optionally substituted with one or more substituents selected from the group consisting of: halogen, aryl, substituted aryl, heterocyclic, substituted heterocyclic, —O—R$_5$ and —NR$_5$R$_6$, where $R_5$ and $R_6$ are as previously defined.

3. A compound according to claim 2, where $R_1$ and $R_2$ taken together are=O.

4. A compound according to claim 3, where $R_4$ is hydrogen.

5. A compound according to claim 1, where $R_4$ is selected from the group consisting of:
(1) $C_1$–$C_6$-alkyl, optionally substituted with one or more substitutents selected from the group consisting of: halogen, aryl, substituted aryl, heterocyclic, substituted heterocyclic, —O—R$_5$ and —NR$_5$R$_6$, where $R_5$ and $R_6$ are as defined in claim 1;
(2) $C_2$–$C_6$-alkenyl, optionally substituted with one or more substituents selected from the group consisting of halogen, aryl, substituted aryl, heterocyclic, substituted heterocyclic, —O—R$_5$ and —NR$_5$R$_6$, where $R_5$ and $R_6$ are as previously defined; and
(3) $C_2$–$C_6$-alkynyl, optionally substituted with one or more substituents selected from the group consisting of halogen, aryl, substituted aryl, heterocyclic, substituted heterocyclic, —O—R$_5$ and —NR$_5$R$_6$, where $R_5$ and $R_6$ are as previously defined.

6. A compound according to claim 5, where $R_1$ and $R_2$ taken together are=O.

7. A compound according to claim 6, where $R_3$ is hydrogen.

8. A compound as defined in claim 1 which is selected from the group consisting of:
Compound of Formula I: A=—CHO, B=—CH$_2$—N(CH$_3$)$_2$, $R_1$ and $R_2$ taken together are=O, $R_3$=H, $R_4$=H and $R^P$=H;
Compound of Formula I: A=—CHO, B=—CH$_2$—NH—CH$_2$CH$_2$Phenyl, $R_1$ and $R_3$ taken together are=O, $R_3$=H, $R_4$=H and $R^P$=H;
Compound of Formula I: A=—CHO, B=—CH$_2$—N(CH$_3$)—CH$_2$CH$_2$Phenyl, $R_1$ and $R_2$ taken together are=O, $R_3$=H, $R_4$=H and $R^P$=H;
Compound of Formula I: A=—CHO, B=—CH$_2$—NH—CH$_2$CH$_2$-(2-pyridyl) $R_1$ and $R_2$ taken together are=O, $R_3$=H, $R_4$=H and $R^P$=H;
Compound of Formula I: A=—CHO, B=—CH$_2$—N(CH$_3$)$_2$, $R_1$ and $R_2$ taken together are=O, $R_3$=H, $R_4$=CH$_3$CHCH-(3-quinolyl) and $R^P$=H;
Compound of Formula I: A=CHO, B=morpholyl, $R_1$ and $R_2$ taken together are=O, $R_3$=H, $R_4$=CH$_2$CC-(3-quinolyl) and $R^P$=H;
Compound of Formula I: A=CHO, B=morpholyl, $R_1$ and $R_2$ taken together are=O, $R_3$=H, $R_4$=CH$_2$CHCH-(3-quinolyl) and $R^P$=H;

Compound of Formula I: A=CHO, B=morpholyl, $R_1$ and $R_2$ taken together are=O, $R_3$=H, $R_4$=CH$_2$CH$_2$CH$_2$-(3-quinolyl) and $R^P$=H;

Compound of Formula I: A=CHO, B=morpholyl, $R_1$ and $R_2$ taken together are=O, $R_3$=H, $R_4$=CH$_2$CC-(5-pyrimidyl) and $R^P$=H;

Compound of Formula I: A=CHO, B=morpholyl, $R_1$ and $R_2$ taken together are=O, $R_3$=H, $R_4$=CH$_2$CHCH-(5-pyrimidyl) and $R^P$=H; Compound of Formula I: A=CHO, B=morpholyl, $R_1$ and $R_2$ taken together are=O, $R_3$=H, $R_4$=CH$_2$CH$_2$CH$_2$-(5-pyrimidyl) and $R^P$=H;

Compound of Formula I: A=CHO, B=morpholyl, $R_1$ and $R_2$ taken together are=O, $R_3$=H, $R_4$=CH$_2$CCCH$_2$-(phenyl) and $R^P$=H;

Compound of Formula I: A=CHO, B=morpholyl, $R_1$ and $R_2$ taken together are=O, $R_3$=H, $R_4$=CH$_2$CHCHCH$_2$-(phenyl) and $R^P$=H;

Compound of Formula I: A=CHO, B=morpholyl, $R_1$ and $R_2$ taken together are=O, $R_3$=H, $R_4$=CH$_2$CH$_2$CH$_2$CH$_2$-(phenyl) and $R^P$=H;

Compound of Formula I: A=CHO, B=morpholyl, $R_1$ and $R_2$ taken together are=O, $R_3$=H, $R_4$=CH$_2$CCCH$_2$-(fluorophenyl) and $R^P$=H;

Compound of Formula I: A=CHO, B=morpholyl, $R_1$ and $R_2$ taken together are=O, $R_3$=H, $R_4$=CH$_2$CHCHCH$_2$-(4-fluorophenyl) and $R^P$=H;

Compound of Formula I: A=CHO, B=morpholyl, $R_1$ and $R_2$ taken together are=O, $R_3$=H, $R_4$=CH$_2$CH$_2$CH$_2$CH$_2$-(4-fluorophenyl) and $R^P$=H;

Compound of Formula I: A=CHO, B=morpholyl, $R_1$ and $R_2$ taken together are=O, $R_3$=H, $R_4$=CH$_2$CCCH$_2$-(3-quinolyl) and $R^P$=H;

Compound of Formula I: A=CHO, B=morpholyl, $R_1$ and $R_2$ taken together are=O, $R_3$=H, $R_4$=CH$_2$CHCHCH$_2$-(3-quinolyl) and $R^P$=H;

Compound of Formula I: A=CHO, B=morpholyl, $R_1$ and $R_2$ taken together are=O, $R_3$=H, $R_4$=CH$_2$CH$_2$CH$_2$CH$_2$-(3-quinolyl) and $R^P$=H;

Compound of Formula I: A=CHO, B=morpholyl, $R_1$ and $R_2$ taken together are=O, $R_3$=H, $R_4$=CH$_2$CC-(2-pyridyl) and $R^P$=H;

Compound of Formula I: A=CHO, B=morpholyl, $R_1$ and $R_2$ taken together are=O, $R_3$=H, $R_4$=CH$_2$CHCH-(2-pyridyl) and $R^P$=H;

Compound of Formula I: A=CHO, B=morpholyl, $R_1$ and $R_2$ taken together are=O, $R_3$=H, $R_4$=CH$_2$CH$_2$CH$_2$-(2-pyridyl) and $R^P$=H;

Compound of Formula I: A=CHO, B=morpholyl, $R_1$ and $R_2$ taken together are=O, $R_3$=H, $R_4$=CH$_2$CC-(3-pyridyl) and $R^P$=H;

Compound of Formula I: A=CHO, B=morpholyl, $R_1$ and $R_2$ taken together are=O, $R_3$=H, $R_4$=CH$_2$CHCH-(3-pyridyl) and $R^P$=H;

Compound of Formula I: A=CHO, B=morpholyl, $R_1$ and $R_2$ taken together are=O, $R_3$=H, $R_4$=CH$_2$CH$_2$CH$_2$-(3-pyridyl) and $R^P$=H;

Compound of Formula I: A=CHO, B=CH$_2$F, $R_1$ and $R_2$ taken together are=O, $R_3$=H, $R_4$=CH$_2$CC-(3-quinolyl) and $R^P$=H;

Compound of Formula I: A=CHO, B=CH$_2$F, $R_1$ and $R_2$ taken together are=O, $R_3$=H, $R_4$=CH$_2$CHCH-(3-quinolyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$-(3-quinolyl) and $R^P$=H;

Compound of Formula I: A=CHO, B=CH$_2$F, $R_1$ and $R_2$ taken together are=O, $R_3$=H, $R_4$=CH$_2$CC-(5-pyrimidyl) and $R^P$=H;

Compound of Formula I: A=CHO, B=CH$_2$F, $R_1$ and $R_2$ taken together are=O, $R_3$=H, $R_4$=CH$_2$CHCH-(5-pyrimidyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$-(5-pyrimidyl) and $R^P$=H;

Compound of Formula I: A=CHO, B=CH$_2$F, $R_1$ and $R_2$ taken together are=O, $R_3$=H, $R_4$=CH$_2$CCCH$_2$-(phenyl) and $R^P$=H;

Compound of Formula I: A=CHO, B=CH$_2$F, $R_1$ and $R_2$ taken together are=O, $R_3$=H, $R_4$=CH$_2$CHCHCH$_2$-(phenyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$CH$_2$-(phenyl) and $R^P$=H;

Compound of Formula I: A=CHO, B=CH$_2$F, $R_1$ and $R_2$ taken together are=O, $R_3$=H, $R_4$=CH$_2$CCCH$_2$-(4-fluorophenyl) and $R^P$=H;

Compound of Formula I: A=CHO, B=CH$_2$F, $R_1$ and $R_2$ taken together are=O, $R_3$=H, $R_4$=CH$_2$CHCHCH$_2$-(4-fluorophenyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$CH$_2$-(4-fluorophenyl) and $R^P$=H;

Compound of Formula I: A=CHO, B=CH$_2$F, $R_1$ and $R_2$ taken together are=O, $R_3$=H, $R_4$=CH$_2$CCCH$_2$-(3-quinolyl) and $R^P$=H;

Compound of Formula I: A=CHO, B=CH$_2$F, $R_1$ and $R_2$ taken together are=O, $R_3$=H, $R_4$=CH$_2$CHCHCH$_2$-(3-quinolyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$CH$_2$-(3-quinolyl) and $R^P$=H;

Compound of Formula I: A=CHO, B=CH$_2$F, $R_1$ and $R_2$ taken together are=O, $R_3$=H, $R_4$=CH$_2$CC-(2-pyridyl) and $R^P$=H;

Compound of Formula I: A=CHO, B=CH$_2$F, $R_1$ and $R_2$ taken together are=O, $R_3$=H, $R_4$=CH$_2$CHCH-(2-pyridyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$-(2-pyridyl) and $R^P$=H;

Compound of Formula I: A=CHO, B=CH$_2$F, $R_1$ and $R_2$ taken together are=O, $R_3$=H, $R_4$=CH$_2$CC-(3-pyridyl) and $R^P$=H;

Compound of Formula I: A=CHO, B=CH$_2$F, $R_1$ and $R_2$ taken together are=O, $R_3$=H, $R^4$=CH$_2$CHCH-(3-pyridyl) and $R^P$=H;

Compound of Formula I: A=CHO, B=CH$_2$F, $R_1$ and $R_2$ taken together are=O, $R_3$=H, $R_4$=CH$_2$CH$_2$CH$_2$-(3-pyridyl) and $R^P$=H;

Compound of Formula I: A=CHO, B=CN, $R_1$ and $R_2$ taken together are=O, $R_3$=H, $R_4$=CH$_2$CC-(3-quinolyl) and $R^P$=H;

Compound of Formula I: A=CHO, B=CN, $R_1$ and $R_2$ taken together are=O, $R_3$=H, $R_4$=CH$_2$CHCH-(3-quinolyl) and $R^P$=H;

Compound of Formula I: A=CHO, B=CN, $R_1$ and $R_2$ taken together are=O, $R_3$=H, $R_4$=CH$_2$CH$_2$CH$_2$-(3-quinolyl) and $R^P$=H;

Compound of Formula I: A=CHO, B=CN, $R_1$ and $R_2$ taken together are=O, $R_3$=H, $R_4$=$CH_2CC$-(5-pyrimidyl) and $R^P$=H;

Compound of Formula I: A=CHO, B=CN, $R_1$ and $R_2$ taken together are=O, $R_3$=H, $R_4$=$CH_2CHCH$-(5-pyrimidyl) and $R^P$=H;

Compound of Formula I: A=CHO, B=CN, $R_1$ and $R_2$ taken together are=O, $R_3$=H, $R_4$=$CH_2CH_2CH_2$-(5-pyrimidyl) and $R^P$=H;

Compound of Formula I: A=CHO, B=CN, $R_1$ and $R_2$ taken together are=O, $R_3$=H, $R_4$=$CH_2CCCH_2$-(phenyl) and $R^P$=H;

Compound of Formula I: A=CHO, B=CN, $R_1$ and $R_2$ taken together are=O, $R_3$=H, $R_4$=$CH_2CHCHCH_2$-(phenyl) and $R^P$=H;

Compound of Formula I: A=CHO, B=CN, $R_1$ and $R_2$ taken together are=O, $R_3$=H, $R_4$=$CH_2CH_2CH_2CH_2$-(phenyl) and $R^P$=H;

Compound of Formula I: A=CHO, B=CN, $R_1$ and $R_2$ taken together are=O, $R_3$=H, $R_4$=$CH_2CCCH_2$-(4-fluorophenyl) and $R^P$=H;

Compound of Formula I: A=CHO, B=CN, $R_1$ and $R_2$ taken together are=O, $R_3$=H, $R_4$=$CH_2CHCHCH_2$-(4-fluorophenyl) and $R^P$=H;

Compound of Formula I: A=CHO, B=CN, $R_1$ and $R_2$ taken together are=O, $R_3$=H, $R_4$=$CH_2CH_2CH_2CH_2$-(4-fluorophenyl) and $R^P$=H;

Compound of Formula I: A=CHO, B=CN, $R_1$ and $R_2$ taken together are=O, $R_3$=H, $R_4$=$CH_2CCCH_2$-(3-quinolyl) and $R^P$=H;

Compound of Formula I: A=CHO, B=CN, $R_1$ and $R_2$ taken together are=O, $R_3$=H, $R_4$=$CH_2CHCHCH_2$-(3-quinolyl) and $R^P$=H;

Compound of Formula I: A=CHO, B=CN, $R_1$ and $R_2$ taken together are=O, $R_3$=H, $R_4$=$CH_2CH_2CH_2CH_2$-(3-quinolyl) and $R^P$=H;

Compound of Formula I: A=CHO, B=CN, $R_1$ and $R_2$ taken together are=O, $R_3$=H, $R_4$=$CH_2CC$-(2-pyridyl) and $R^P$=H;

Compound of Formula I: A=CHO, B=CN, $R_1$ and $R_2$ taken together are=O, $R_3$=H, $R_4$=$CH_2CHCH$-(2-pyridyl) and $R^P$=H;

Compound of Formula I: A=CHO, B=CN, $R_1$ and $R_2$ taken together are=O, $R_3$=H, $R_4$=$CH_2CH_2CH_2$-(2-pyridyl) and $R^P$=H;

Compound of Formula I: A=CHO, B=CN, $R_1$ and $R_2$ taken together are=O, $R_3$=H, $R_4$=$CH_2CC$-(3-pyridyl) and $R^P$=H;

Compound of Formula I: A=CHO, B=CN, $R_1$ and $R_2$ taken together are=O, $R_3$=H, $R_4$=$CH_2CHCH$-(3-pyridyl) and $R^P$=H; and Compound of Formula I: A=CHO, B=CN, $R_1$ and $R_2$ taken together are=O, $R_3$=H, $R_4$=$CH_2CH_2CH_2$-(3-pyridyl) and $R^P$=H.

9. A pharmaceutical composition for treating bacterial infections comprising a therapeutically effective amount of a compound of claim 1 or a pharmaceutically acceptable salt, ester or prodrug thereof in combination with a pharmaceutically acceptable carrier.

10. A method for treating bacterial infections comprising administering to an animal in need of such treatment a pharmaceutical composition comprising a pharmaceutically effective amount of a compound of claim 1 or a pharmaceutically acceptable salt, ester or prodrug thereof.

11. A process for preparing a compound represented by Formula I as defined in claim 1 comprising:

(a) reacting a compound represented by the formula:

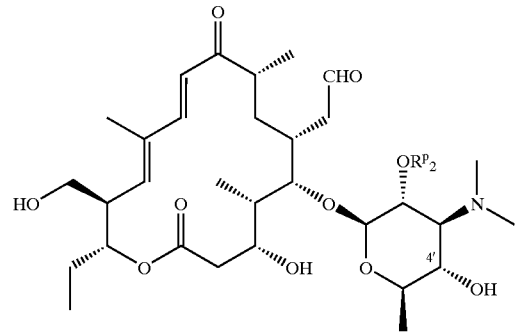

wherein $R^P_2$ is a hydroxy protecting group, with:
i. an acetalating agent at a pH between 1 to 4 in an alcoholic solvent; and
ii. treating with a silylating agent, optionally with the addition of a catalyst in an aprotic solvent at a temperature between 0° C. to 50° C. for 1 to 48 hours to provide a compound represented by the Formula:

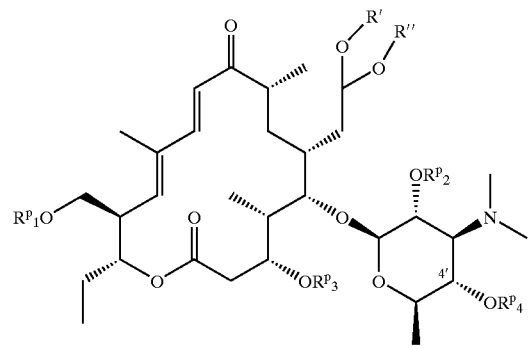

wherein $R^P_1$, $R^P_2$, $R^P_3$ and $R^P_4$ are hydroxy protecting groups, and R' and R" are each $C_1$–$C_6$-alkyl or when taken together are —$CH_2CH_2$— or —$CH_2CH_2CH_2$—;

(b) treating the compound from step (a) with an acid in an organic solvent at a temperature between 0° C. and 50° C. for 1–24 hours to provide a compound represented by the formula:

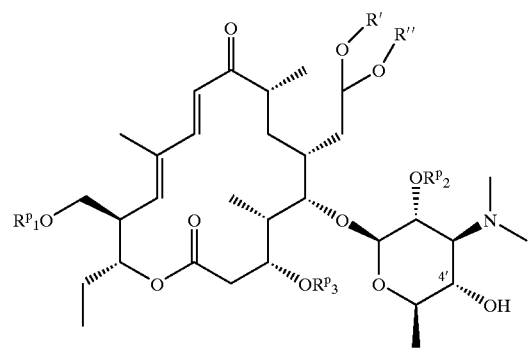

wherein $R^P_1$, $R^P_2$, $R^P_3$, R' and R" are as previously defined;

(c) reacting the compound from step (b) with an alkylating agent represented by the formula $R_4X$, wherein X is a halogen or sulphonyl group and $R_4$ is as defined in claim 1, in the presence of a base in an aprotic solvent at a temperature between −20° C. to 60° C. optionally in the presence of water and a phase transfer catalyst, and then treating with an acid in an organic solvent at a temperature between room temperature to 100° C. for 1 to 48 hours to provide a compound represented by the formula:

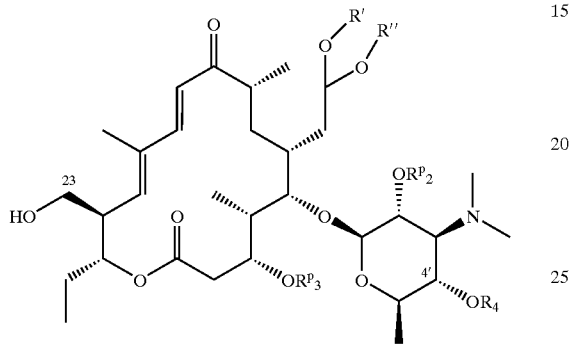

wherein $R^P_2$, $R^P_3$, $R_4$, R' and R" are as previously defined;

(d) treating the compound from step (c) with triphenylphosphine and a halogenating agent or with a sulfonic anhydride or sulfonyl chloride in an aprotic organic solvent at a temperature between −78° C. and 50° C. for 30 minutes to 48 hours, optionally in the presence of an amine base and a catalyst, to provide a compound represented by the formula:

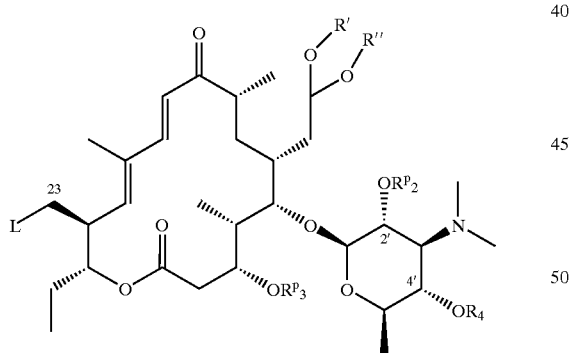

where L is selected from the group consisting of chlorine, bromine, iodine, mesylate and tosylate and $R^P_2$, $R^P_3$, $R_4$, R' and R" are as previously defined; and (e) treating the compound from step (d) with an amine of the formula $NHR_5R_6$, wherein $R_5$ and $R_6$ are as defined in claim 1, at a temperature from 0° C. to 100° C. for 1 to 24 hours, optionally deprotecting the product by:
  i. treating with an aqueous acid in an organic solvent at a temperature from 0° C. to 100° C. for 1 to 24 hours; and
  ii. stirring in methanol at a temperature between room temperature and reflux temperature for 4 to 24 hours;

to provide a compound represented by Formula I wherein A is —CHO, B is —$CH_2$—$NR_5R_6$, $R_1$ and $R_2$ together are O, $R_3$ is H, $R^P$ is H, and $R_4$ is as defined in claim 1.

12. A process for preparing a compound represented by Formula I, as defined in claim 1 comprising:

(a) reacting a compound represented by the Formula:

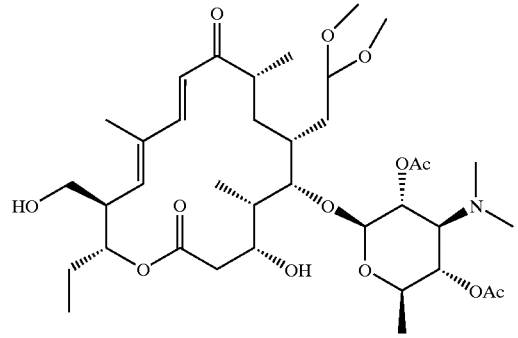

where Ac is —$COCH_3$, in an aprotic organic solvent with a sulfonic anhydride or sulphonyl halide in the presence of an amine base, optionally with a catalyst, between 0° C. and room temperature for 30 minutes to two hours and treating the resulting product with sodium iodide, at a temperature between 0° C. to 100° C. for 1 to 24 hours, to provide a compound represented by the formula:

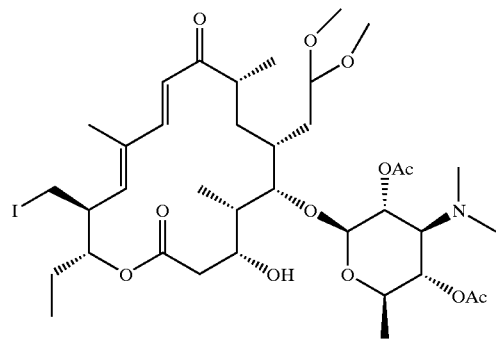

where Ac is as previously defined; and (b) treating the compound from step (a) with an amine of the formula $NHR_5R_6$, where $R_5$ and $R_6$ are as defined in claim 1, at a temperature from 0° C. to 100° C. for 1 to 24 hours, optionally deprotecting the product by:
  i. treating with an aqueous acid in an organic solvent at a temperature from 0° C. to 100° C. for 1 to 24 hours; and
  ii. stirring in methanol at a temperature between room temperature and reflux temperature;

to provide a compound represented by Formula I where A is —CHO, B is —$CH_2$—$NR_5R_6$, $R_1$ and $R_2$ taken together are O, $R_3$ is H, $R^P$ is H, and $R_4$ is H.

13. A process for preparing a compound represented by the formula:

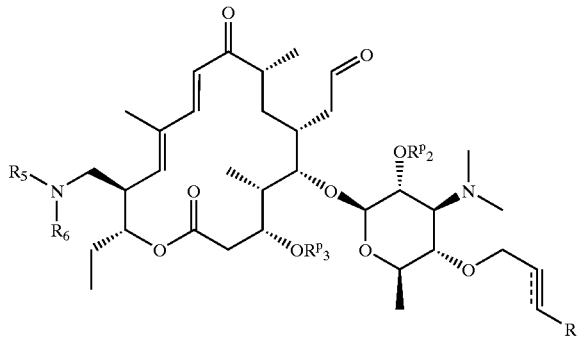

wherein R is aryl, substituted aryl, heteroaryl, or substituted heteroaryl, $R^P_2$ and $R^P_3$ are each independently hydrogen or a hydroxy protecting group and $R_5$ and $R_6$ are as defined in claim 1, comprising:

(a) reacting a compound represented by the formula:

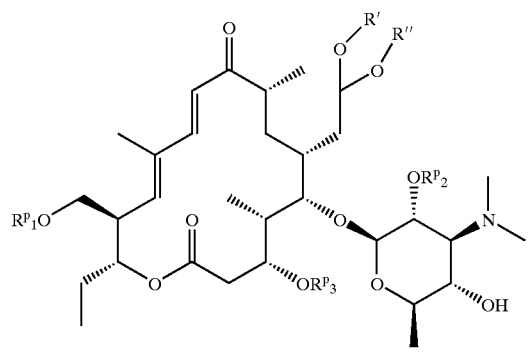

wherein $R^P_1$, $R^P_2$ and $R^P_3$ are hydroxy protecting groups, and R' and R" are each $C_1$–$C_6$-alkyl or when taken together are —$CH_2CH_2$— or —$CH_2CH_2CH_2$—, with a propargyl halide and optionally reducing the product with a borane or stannane reagent to give a vinyl borane or vinyl stannane derivative represented by the formula:

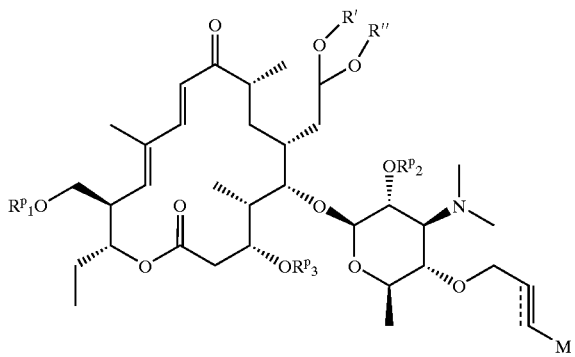

wherein M is hydrogen, $B(OH)_2$ or $SnBu_3$ and $R^P_1$, $R^P_2$, $R^P_3$, R' and R" are as previously defined;

(b) reacting the compound from step (a) with a compound represented by the formula R—X wherein R is aryl, substituted aryl, heteroaryl, or substituted heteroaryl and X is a halide or triflate, in the presence of a palladium catalyst to give a compound represented by the formula:

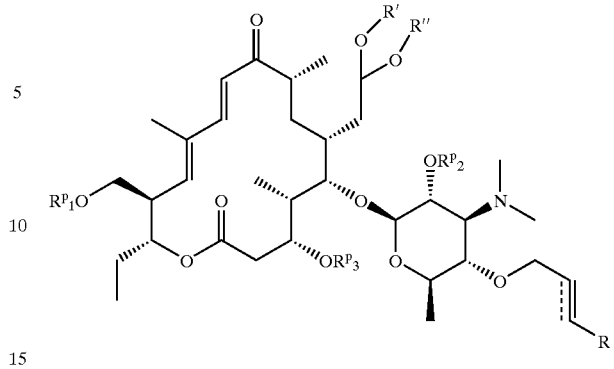

wherein R, $R^P_1$, $R^P_2$, $R^P_3$, R' and R" are as previously defined; and (c) treating the compound from step (b) with an organic acid in an organic solvent at a temperature between room temperature to 100° C. for 1–48 hours to provide a compound represented by the formula:

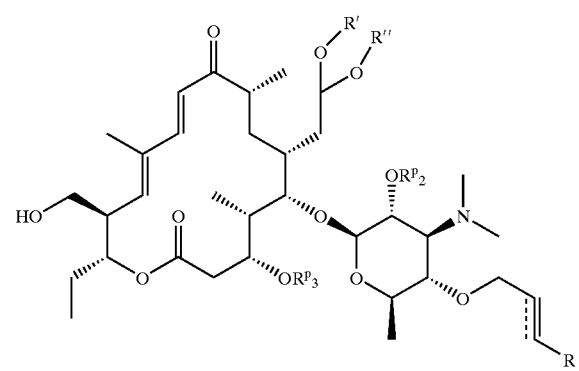

wherein R, $R^P_2$, $R^P_3$, R' and R" are as previously defined;

(d) treating the compound from step (c) with triphenylphosphine and a halogenating agent or with a sulfonic anhydride or sulfonyl chloride in an aprotic organic solvent at a temperature between –78° C. to 50° C. for 30 minutes to 48 hours, optionally in the presence of an amine base and a catalyst, to provide a compound represented by the formula:

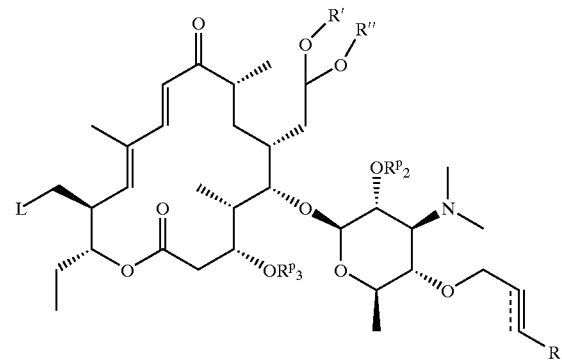

where L is chlorine, bromine, iodine, mesylate or tosylate and $R^P_2$, $R^P_3$, R, R' and R" are as previously defined; and (e) treating the compound from step (d) with an amine of the formula $NHR_5R_6$, where $R_5$ and $R_6$ are as defined in claim 1, at a temperature from 0° C. to 100° C. for 1 to 24 hours, optionally deprotecting the product by:
i. treating with an aqueous acid in an organic solvent at a temperature from 0° C. to 100° C. for 1 to 24 hours; and
ii. stirring in methanol at a temperature between room temperature and reflux temperature for 4 to 24 hours;
to provide a compound represented by the formula:

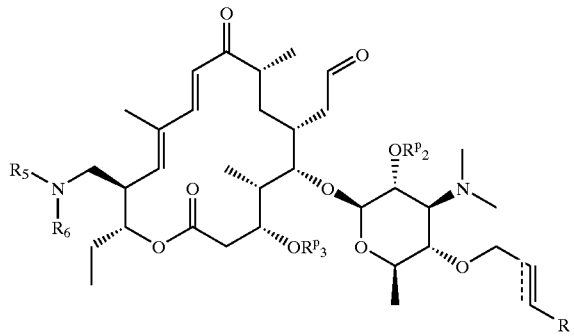

wherein $R^P_2$, $R^P_3$, R, $R_5$ and $R_6$ are as previously defined.

14. A process for preparing a compound represented by the formula:

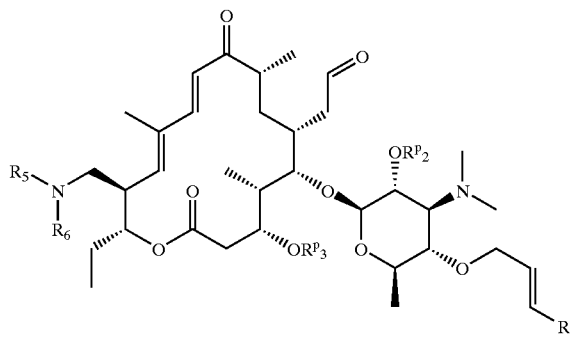

wherein R is aryl, substituted aryl, heteroaryl, or substituted heteroaryl, $R^P_2$, and $R^P_3$ are each independently hydrogen or a hydroxy protecting group, and $R_5$ and $R_6$ are as defined in claim 1, comprising:
(a) reacting a compound represented by the formula:

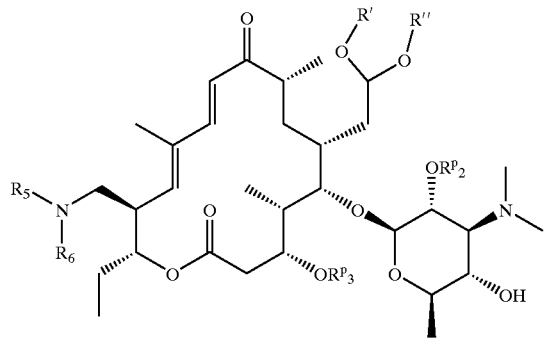

wherein $R^P_2$ and $R^P_3$ are hydroxy protecting groups, and R' and R" are each $C_1$–$C_6$-alkyl or when taken together are —$CH_2CH_2$— or —$CH_2CH_2CH_2$— and $R_5$ and $R_6$ are as defined in claim 1, with a tert-butyl allyl carbonate or an aryl tert-butyl allyl carbonate in the presence of a palladium catalyst to provide a compound represented by the formula:

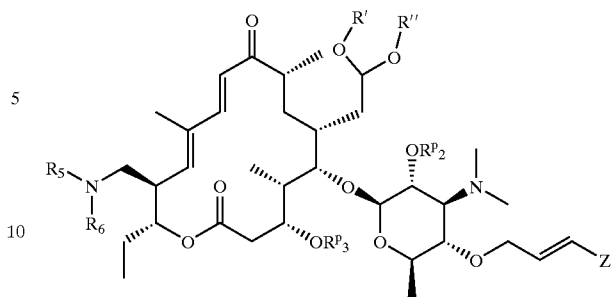

wherein Z is hydrogen or R and where R, $R_5$, $R_6$, $R^P_2$, $R^P_3$, R' and R" are as previously defined;

(b) when Z is hydrogen, reacting the compound from step (a) with a compound represented by the formula R—X where R is aryl, substituted aryl, heteroaryl, or substituted heteroaryl and X is a halide or triflate, in the presence of a palladium catalyst to provide a compound represented by the formula:

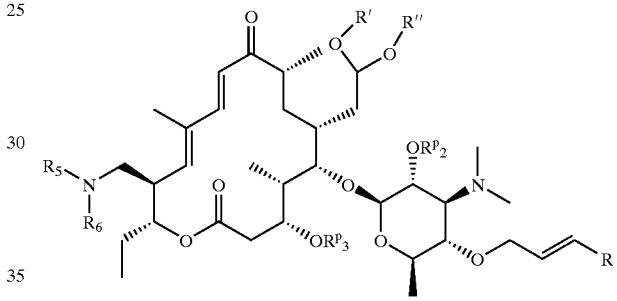

wherein R, $R_5$, $R_6$, $R^P_2$, $R^P_3$, R' and R" are as previously defined. optionally deprotecting the compound from step (a) or (b) by:
i. treating with an aqueous acid in an organic solvent at a temperature from 0° C. to 100° C. for 1 to 24 hours; and
ii. stirring in methanol at a temperature between room temperature and reflux temperature for 24 hours;

to provide a compound represented by the formula:

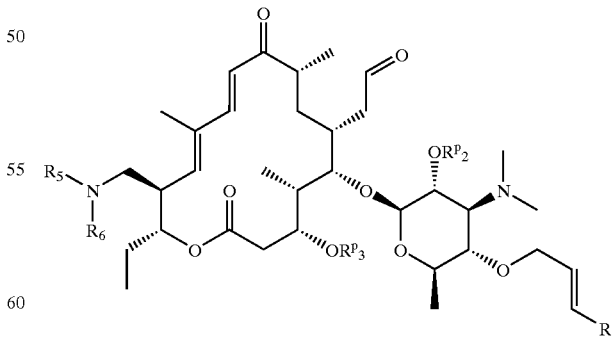

where R, $R_5$, $R_6$, $R^P_2$, and $R^P_3$ are as previously defined.

15. A process for preparing a compound represented by Formula I, as defined in claim 1, comprising:

(a) reacting a compound represented by the formula:

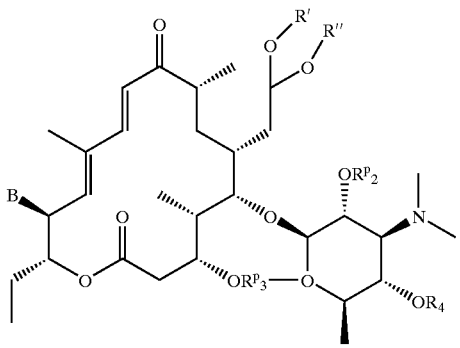

where B and $R_4$ are as defined in claim 1, $R^P_2$ and $R^P_3$ are each independently hydroxy protecting groups, and R' and R" are each $C_1$–$C_6$-alkyl or when taken together are —$CH_2CH_2$— or —$CH_2CH_2CH_2$—, with tetrabutyl ammonium flouride or hydrofluoric acid to provide a compound represented by the formula:

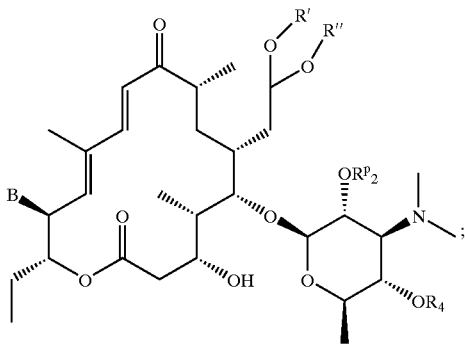

wherein B, $R_4$, $R^P_2$, R' and R" are as previously defined, (b) reacting the compound from step (a) with an alkylating agent in the presence of a base in an aprotic solvent at a temperature between −20° C. and 60° C. to provide a compound of the formula:

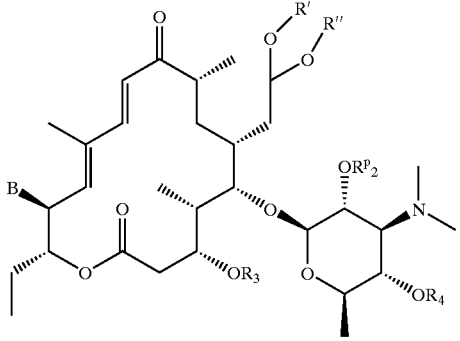

wherein $R_3$ is as defined in claim 1 and B, $R_4$, $R^P_2$, R' and R" are as previously defined, optionally deprotecting the compound from step (b) by:
  i. treating with an aqueous acid in an organic solvent at a temperature between 0° C. and 100° C. for 1 to 24 hours; and
  ii. stirring in methanol at a temperature between room temperature and reflux temperature;

to provide a compound represented by Formula I wherein A is —CHO, $R_1$ and $R_2$ taken together are=O, B, $R_3$ and $R_4$ are as defined in claim 1 and $R_p$ is hydrogen.

16. A process for preparing a compound represented by Formula I, as defined in claim 1, comprising:

(a) reacting a compound represented by the formula:

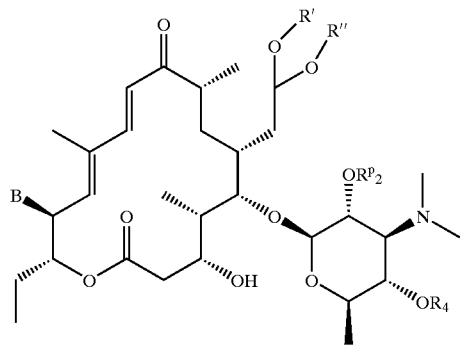

wherein B and $R_4$ are as defined in claim 1, $R^P_2$ is a hydroxy protecting group, and R' and R" are each $C_1$–$C_6$-alkyl or when taken together are —$CH_2CH_2$— or —$CH_2CH_2CH_2$—, with a propargyl halide and optionally reducing the product with a borane or stannane reagent to give a vinyl borane or vinyl stannane derivative represented by the Formula:

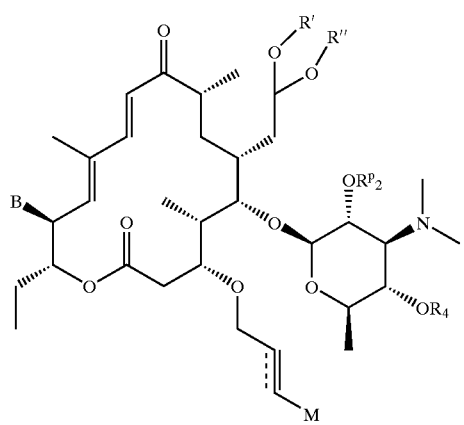

wherein M is hydrogen, $B(OH)_2$ or $SnBu_3$ and B, $R_4$, $R^P_2$, R' and R" are as previously defined;

(b) reacting the compound from step (a) with a compound represented by the formula R—X where R is aryl, substituted aryl, heteroaryl, or substituted heteroaryl, and X is a halide or triflate, in the presence of a palladium catalyst to give a compound represented by the formula:

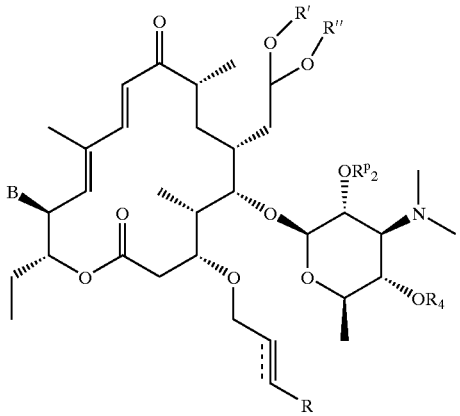

wherein B, R, $R_4$, $R^P_2$, R' and R" are as previously defined, optionally deprotecting the compound from step (b) by:
i. treating with an aqueous acid in an organic solvent at a temperature between 0° C. and 100° C. for 1 to 24 hours; and
ii. stirring in methanol at a temperature between room temperature and reflux temperature;

to provide a compound represented by Formula I wherein A is —CHO, $R_1$ and $R_2$ taken together are O, $R_3$ is —CH$_2$CHCH—R or —CH$_2$C=C—R, R is as previously defined, B and $R_4$ are as defined in claim 1, and $R^P$ is hydrogen.

17. A process for preparing a compound represented by Formula I, as defined in claim 1 comprising:

(a) reacting a compound represented by the formula:

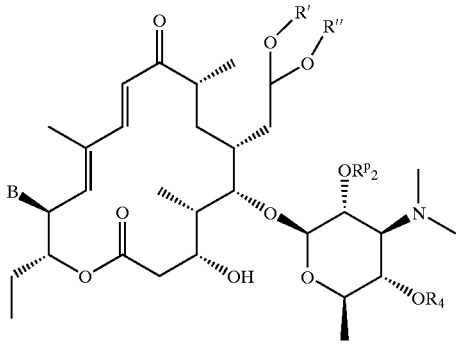

wherein B and $R_4$ are as defined in claim 1, $R^P_2$ is a hydroxy protecting group, and R' and R" are each $C_1$-$C_6$-alkyl or when taken together are —CH$_2$CH$_2$— or —CH$_2$CH$_2$CH$_2$—, with an allyl halide to give a compound represented by the formula:

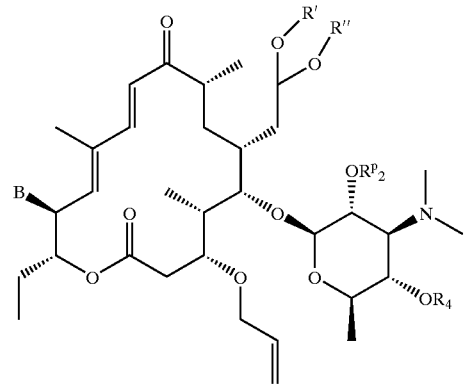

wherein B, $R_4$, $R^P_2$, R' and R" are as previously defined;

(b) reacting the compound from step (a) with a vinyl-R derivative, where R is aryl, substituted aryl, hetroaryl or substituted heteroaryl, using a ruthenium catalyst, to provide a compound represented by the formula:

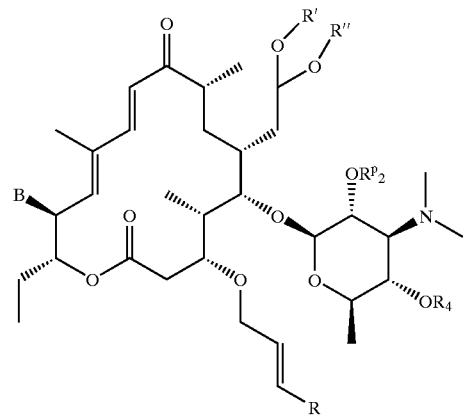

wherein B, R, $R_4$, $R^P_2$, R' and R" are as previously defined, optionally deprotecting the compound from step (b) by;
i. treating with an aqueous acid in an organic solvent at a temperature between 0° C. and 100° C. for 1 to 24 hours; and
ii. stirring in methanol at a temperature between room temperature and reflux temperature;

to provide a compound represented by Formula I wherein A is —CHO, $R_1$ and $R_2$ taken together are O, $R_3$ is —CH$_2$CHCH—R, R is as previously defined, B and $R_4$ are as defined in claim 1, and $R^P$ is hydrogen.

* * * * *